(12) United States Patent
Yufa

(10) Patent No.: US 7,439,855 B1
(45) Date of Patent: Oct. 21, 2008

(54) METHOD AND WIRELESS COMMUNICATING APPARATUS FOR ANALYSIS OF ENVIRONMENT

(76) Inventor: Aleksandr L. Yufa, 698 Cypress Ave., Colton, CA (US) 92324

( * ) Notice: Subject to any disclaimer, the term of this patent is extended or adjusted under 35 U.S.C. 154(b) by 0 days.

(21) Appl. No.: 11/128,780

(22) Filed: May 13, 2005

(51) Int. Cl.
*G08B 1/08* (2006.01)
*G01N 15/02* (2006.01)
*G01N 21/00* (2006.01)

(52) U.S. Cl. .............................. 340/539.1; 340/539.22; 340/539.26; 356/336; 356/338; 356/339

(58) Field of Classification Search . 340/539.1–539.29, 340/870.01–870.17; 356/336, 338–339
See application file for complete search history.

(56) References Cited

U.S. PATENT DOCUMENTS

| | | | | |
|---|---|---|---|---|
| 5,351,118 A | * | 9/1994 | Spinell | 356/72 |
| 5,446,445 A | * | 8/1995 | Bloomfield et al. | 340/521 |
| 5,781,291 A | * | 7/1998 | So et al. | 356/338 |
| 5,946,091 A | | 8/1999 | Yufa | |
| 6,078,040 A | * | 6/2000 | Endo et al. | 250/222.2 |
| 6,315,955 B1 | * | 11/2001 | Klein | 422/73 |
| 6,346,983 B1 | | 2/2002 | Yufa | |
| 6,437,692 B1 | * | 8/2002 | Petite et al. | 340/540 |
| 6,573,991 B1 | * | 6/2003 | Debreczeny et al. | 356/336 |

FOREIGN PATENT DOCUMENTS

JP H4-12248 1/1992

* cited by examiner

*Primary Examiner*—Benjamin C Lee

(57) ABSTRACT

The improved methods and apparatus for analysis of environment provide wireless communication of the environmental analyzers, e.g. such as particle monitoring (counting and measuring) instruments. The improved apparatus includes at least one of a plurality of environment monitoring systems and at least one of a plurality of remote control systems, each of which comprises the wireless communicating device and control/processing device. Also the improved apparatus includes the selectable channel flow system for the assayed environment which intersects a light (laser) beam or a ray within monitoring region of the monitoring device of the improved apparatus. The selection of the channel is provided by the valving device coupled with the inlet filtrating device.

14 Claims, 18 Drawing Sheets

METHOD AND WIRELESS COMMUNICATING APPARATUS FOR ANALYSIS OF ENVIRONMENT

FIELD OF THE INVENTION

This invention relates to the apparatus for analysis of environment such as air, gas and/or liquid/fluid, water and, more particularly, can be related to contamination control apparatus, such particle quantity counting and particle size measuring.

BACKGROUND OF THE INVENTION

The apparatus for analysis of environment, for instance, such as air (gas) particle quantity counting and particle size measuring, or liquid/fluid (water) particle/contamination size measuring and quantity counting, or airborne (gas) particle and/or liquid/fluid (water) contamination sampling, or airborne (gas) particle and/or liquid/fluid (water) contamination concentration analysis, and the other (hereinafter such apparatus will be mentioned as an environmental analyzer, and the air, gas, liquid/fluid, water, etc. will be mentioned as environment) is known.

Such apparatus for analysis of environment, providing airborne, gas and/or liquid/fluid, water quality analysis (analysis of environment) generally comprises a particle detecting means and a data (signals, information) processing means, and can be of two kinds: portable or remote. The portable apparatus for analysis of environment commonly is a portable unit including a particle detecting means, processor/controller, display, sometimes printer, and front panel with the organs for manual control, and requires the presence of operator (operator-in-site) for control of the unit on site and print out the results for further consideration. The remote apparatus for analysis of environment mostly uses the long wire (long cable, e.g. 100 yards and longer) connection between remote particle detecting means and central data processing and control unit.

For example, it is well known, that integrated circuits (chips) and semiconductors have been produced in "clean rooms". The air in such "clean rooms" should be very well cleaned. The continuing tendencies of improvement in the circuit integration and degree of microminiaturization require corresponding improvements of the environment in "clean rooms" and efficiency and sensitivity of the contamination measuring devices. The sensitivity of the counting and measuring devices should provide the detection of the particles/contaminations (hereinafter particles/contaminations will be mentioned as particle) at least as small as 0.085 μm (micron) or smaller. Such rate requires minimum distortions of the signals. Also, the measurements should be done in the different places of the semiconductor production areas and sometimes in the areas with the difficult access and approach. The same is, for instance, regarding the pharmaceutical, biological industries, etc. where the high environmental condition is required too.

It is also known, that all long wire (long cable) connections in electronic apparatus are a source of the electromagnetic noise, which can create interference in the semiconductor production area, and a distortion of the signals, creating an insufficient signal to noise ratio, thereby limiting the sensitivity and efficiency of the environmental analyzers.

Another deficiency of the environmental analyzers with the long cable connection between the remote sensor and the data processing unit is a limited mobility, because of the cable. Therefore, the U.S. Pat. No. 6,346,983 describes the wireless communicating environmental analyzer able to analyze air, gas and/or liquid/fluid, water, etc. The method, providing wireless communication between at least one of a plurality of remote detecting systems (sensor) and data processing and control system (computer), is realized by an apparatus including a wireless communication means. The apparatus also comprises a remote detecting system comprising a particle detecting system, comprising a particle detecting means connected to a signal processing system, which is connected to a conversion system. Also, the remote detecting system comprises a wireless communication means, including an aerial means connected to a transmitting means and to a receiving means of the transmitting-receiving means. The conversion means of the particle detecting system is connected to the transmitting means and to receiving means. The apparatus by the mentioned above patent also includes the data processing and control system comprising a wireless communication means and processing system, comprising a processing means, a conversion means and a terminal means. The wireless communication means can include an aerial means connected to a transmitting-receiving means. The transmitting-receiving means connected to the conversion means of the processing system. The terminal means can include a displaying means, a floppy disk means, a compact disk means, a printing means and a control panel (for example, a computer's keyboard, communication control device, etc.), which are connected to each other, to the microprocessor means and to the conversion means by a multiplexed bus (a data bus and an address bus /both are not shown/ or any other communication means and principles can be used instead of the multiplexed bus). It is understandable from the described prior art, that the control panel can include devices, instruments, means, etc. providing any and all needed controls of the data processing, displaying of the data and information, analyzing/detecting processes and operation of the remote detecting system(s), and control of communication (remote wirelessly and/or non-wirelessly, etc.) between appropriate means and systems of the apparatus, etc. It is also understandable from the mentioned above patent, that the wireless communication means can be appropriately built-in the remote detecting unit (e.g. sensor) and data processing and control system (e.g. computer, etc.) respectively or the wireless communication means can be appropriately connected to the remote detecting unit and data processing and control system respectively (for example, the wireless communication means can be the adapter-style devices directly connected to the outside connectors of the remote detecting unit and data processing and control system respectively) or can be presented by the adapters (separate devices) connected to the data processing and control system and to remote detecting unit respectively through a short cables (e.g. remote adapter/device, etc.). The wireless communication for the described prior art can be provided in compliance with any wireless principles, for example, such as radio (e.g. digital, FM, telemetering, digital telemetering, etc.), satellite (e.g. Internet), and even voice/sound control, etc. Each of the both major parts of the described apparatus (i.e. data processing and control system, and remote detecting system) can use two-way wireless communication means, each of which includes transmitting-receiving means comprising the transmitting means and receiving means.

The control signal(s), controlling the remote detecting system, from the control panel follow to the processing system. The control signals processed by the processing means, via the conversion means of the processing system follow to the transmitting-receiving means of the wireless communication means. The control signal can provide, for example, possibility to switch "on/off", to switch "run/stop", to select and change the particle counting and measuring channels, to provide remote sensor diagnostics, to switch the mode (regime) from particle counting and measuring to concentration determination, to select and change the modes for the particle flow velocity, environmental temperature and/or humidity determination, etc. The signals from the transmitting-receiving means follow to the aerial means. The wireless communication means of the data processing and control system communicates with the wireless communication means of the remote detecting system. The signal(s) received by the aerial means of the wireless communication means of the remote unit follow via the receiving means of the transmitting-receiving means and conversion system of the detecting system to the signal processing system. The processed signals control the detecting means, which, for example, starts to assay environment (hereinafter the assayed environment will be mentioned as assayed specimen), analyze, process the result(s) of the analysis, form data containing information about analyzed environment, etc. The appropriately processed and converted data (information) is transmitted to the data processing and control system for final processing and displaying in the convenient form (e.g. by the displaying means or printed by the printing means, etc.) to the operator for consideration. It is well understandable, that the data can include the information (signals), for instance, regarding battery condition (e.g. "low battery" signal if the battery is presented in the remote detecting system /the power supply of the some remote detecting system can be, for example, provided by alternative current source, etc.), some alarm (warning) signals (e.g. particle concentration warning, hydrogen concentration alarm, etc.), etc.

Thus, there is a great need in the art for the improved method and environment analyzing apparatus to provide more mobility of the control means controlling the wireless communication between the appropriate systems of the environment analyzing apparatus, and to provide the detecting means with the precise flow system for the assayed specimen.

OBJECT AND ADVANTAGES OF THE INVENTION

Accordingly, several objects and advantages of the present invention are to provide an improved method and wireless communicating environmental analyzer.

It is the object of the invention to increase efficiency of the wireless communication and control.

It is another object of the invention to increase the control means mobility.

It is further object of the invention to increase the precision and efficiency of the assayed specimen flow system.

It is still further object of the invention to eliminate the presence of the operator in the clean rooms by using wireless communicating remote control outside of the clean rooms.

Still, further objects and advantages will become apparent from a consideration of the ensuing description accompanying drawings.

SUMMARY OF THE INVENTION

Figure 1:
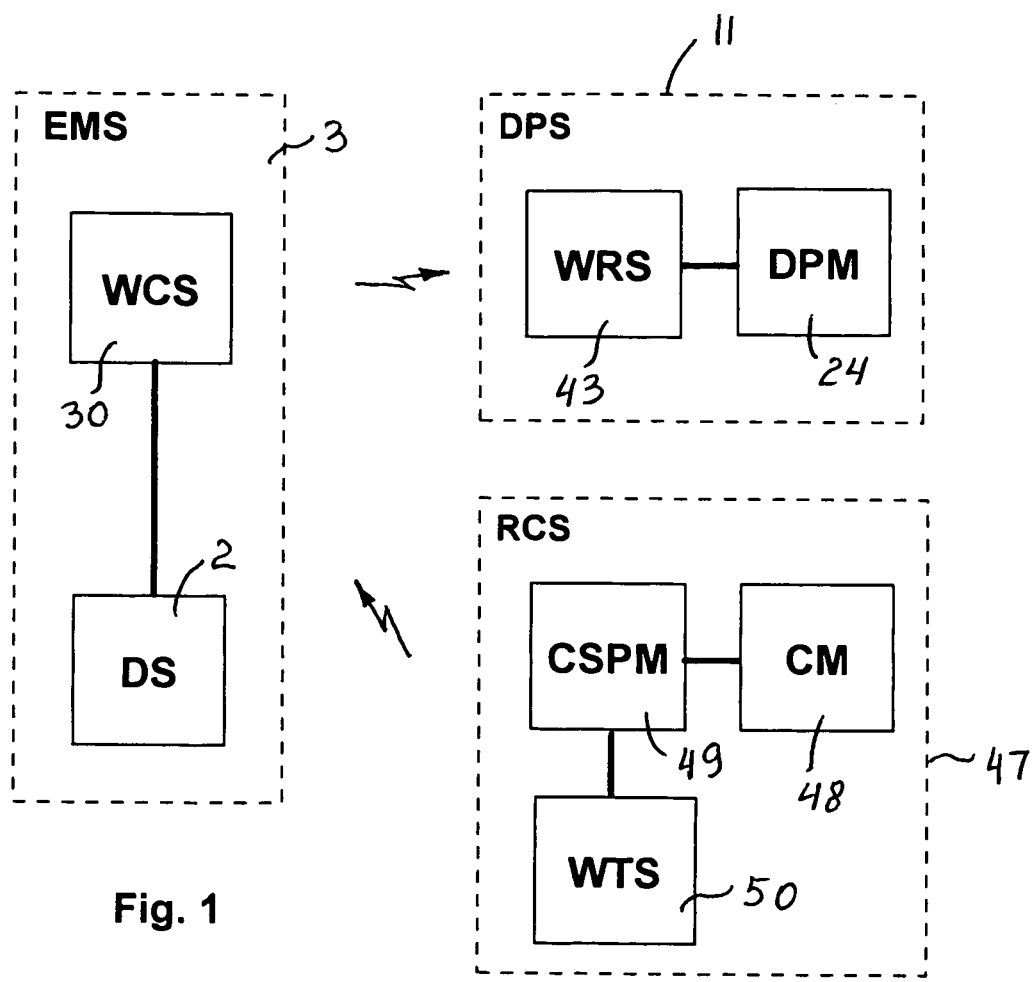
FIG. 1 is a simplified structural block diagram presentation of the first wireless communication variant.

The invention provides a methods and wireless communicating apparatus for analysis of environment.

The improved apparatus for analysis of environment, providing airborne, gas and/or liquid/fluid, water quality analysis generally comprises an environment monitoring (sensing, detecting) system and a data (signals, information) processing system. The portable apparatus for analysis of environment generally includes an environment monitoring (sensing, detecting) system (as a portable unit) comprising the detecting system, initial signal processing means, signal and data processing and control system, and a remote control system wireless communicating with the environment monitoring system (more specifically, the remote control system provides the wireless control of the environment monitoring system). The remote apparatus for analysis of environment generally includes an environment monitoring (sensing, detecting) system (as a remote unit), comprising the detecting system, initial signal processing means, signal and data processing and control system, central data processing system, and remote control system wireless communicating with the environment monitoring system and central data processing system.

In detail, the invention provides a methods and wireless communicating apparatus for analysis of environment including a wireless communication system/means, intended for wireless communication of at least one of a plurality of environment monitoring systems (as a remote units) with at least one of a plurality of data processing systems, and wireless control of at least one of a plurality of environment monitoring systems (as a remote units) by the remote control system, or including a wireless communication system/ means, intended for wireless communication and control of the environment monitoring systems (as a portable units) by the remote control system.

The improved methods and environment analyzing apparatus provide an airborne (gas) and/or liquid/fluid (water) contamination analysis providing the wireless control by the wireless communicating remote control system.

An improved apparatus, realizing the improved methods, generally includes a environment monitoring system, comprising a detecting system and a wireless transmitting-receiving means, a data processing system and a remote control system. The control signal(s) from a remote control system are transmitted by the wireless transmitting system of the remote control system to the wireless receiving means of the wireless transmitting-receiving system of the environment monitoring system. Further the signals from wireless receiving system of the environment monitoring system via the appropriate conversion system of the detecting system follow to the signal processing and control system of the detecting system. The signal processing and control system provides a control (for example, mode/regime switching, turn-on/turn-off operations, etc.) of the environment assaying control means (for example, air/liquid pumps (blower, etc.), flowmeter, humidity and/or temperature meters, etc.), which by tubular means transfer an assayed specimen to the monitoring means. The monitoring means provides monitoring of the assayed specimen and forms the output, which is effectively indicative of the assayed specimen at least one of a plurality of characteristic(s) that are needed for operator's consideration. This output is processed by the signal processing and control system, which appropriately forms a data containing information about that characteristic(s). The data conversed by conversion system via wireless transmitting means of the wireless transmitting-receiving means of the environment monitoring system is transmitted to the wireless receiving system of the data processing system. The received data is further appropriately conversed and processed by the data processing means. The processed data (the result) can be in the appropriate and/or any desirable form presented (e.g. displayed, etc.) to the operator (e.g. to a computer operator, etc.).

DESCRIPTION OF THE PREFERRED EMBODIMENTS

Here the description of an improved apparatus will be done in statics (as if the components of the improved apparatus are suspended in the space) with description of their relative locations and connections to each other. The description of the improved methods and functional operations of an improved apparatus will be done hereinafter.

FIG. 1 illustrates a structure of the wireless communicating environmental analyzer (apparatus) including a environment monitoring system 3, comprising a detecting system 2 connected to a wireless communication system 30 of the environment monitoring system 3, a data processing system 11, comprising a data processing means 24 connected to a wireless receiving system 43 of the data processing system 11, and a remote control system 47, comprising a control means 48, a control processing means 49 and a wireless transmitting system 50. Each wireless communication system can comprise a wireless transmitting means and wireless receiving means (the wireless communication system can include the aerial means if appropriate [e.g. if the radio control principles are used instead of the beam/ray control principles]). Also, the retransmitters/repeaters (not shown) can be used if necessary. The wireless receiving system comprises a wireless receiving means (the wireless receiving system can include the aerial means (not shown) if appropriate [e.g. if the radio principles are used instead of the beam/ray principles]), and the wireless transmitting system comprises a wireless transmitting means (the wireless transmitting system can include the aerial means (not shown) if appropriate [e.g. if the radio principles are used instead of the beam/ray principles]).

Figure 2:
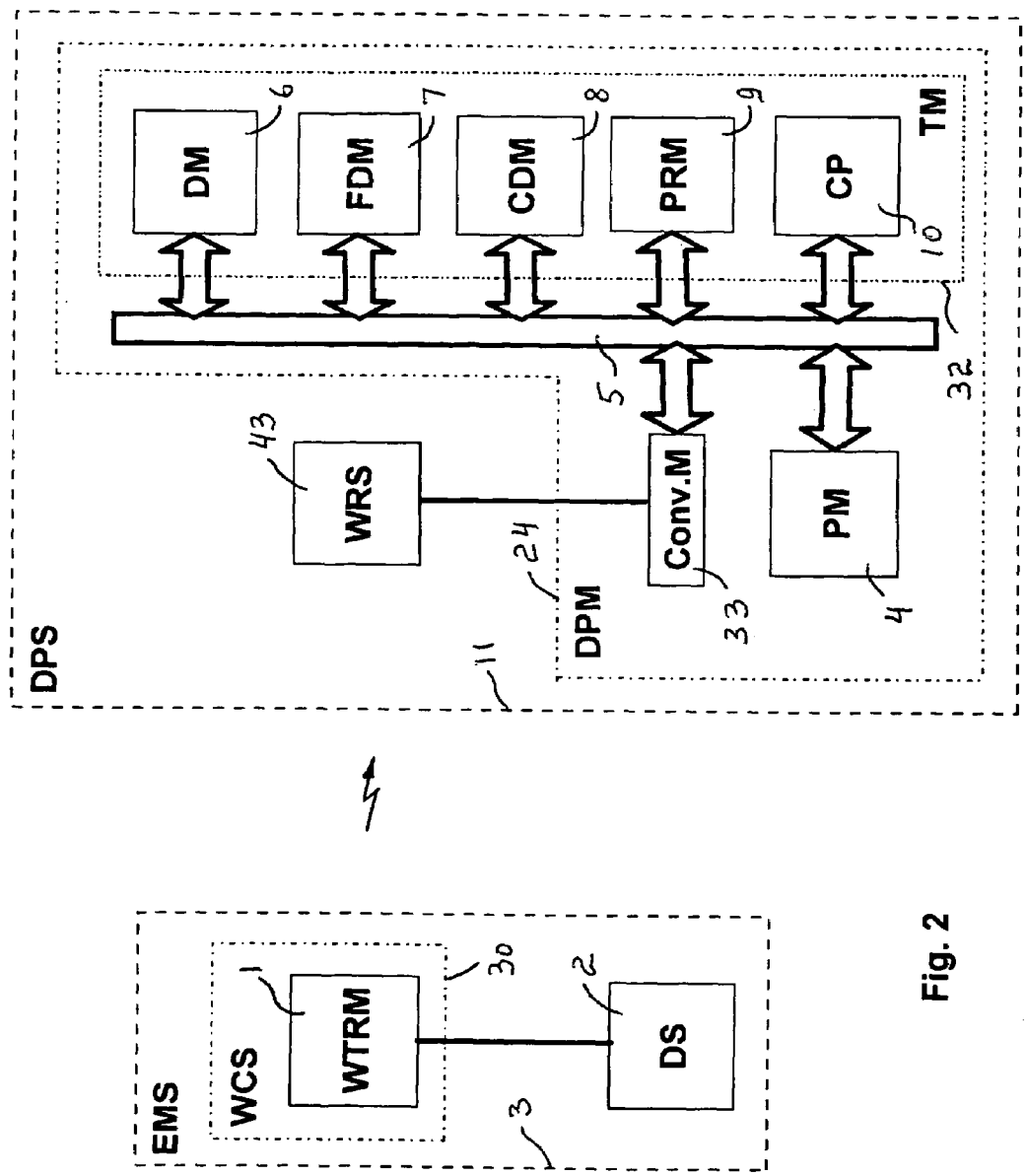
FIG. 2 is a simplified first functional block diagram of the first wireless communication variant.
Figure 3:
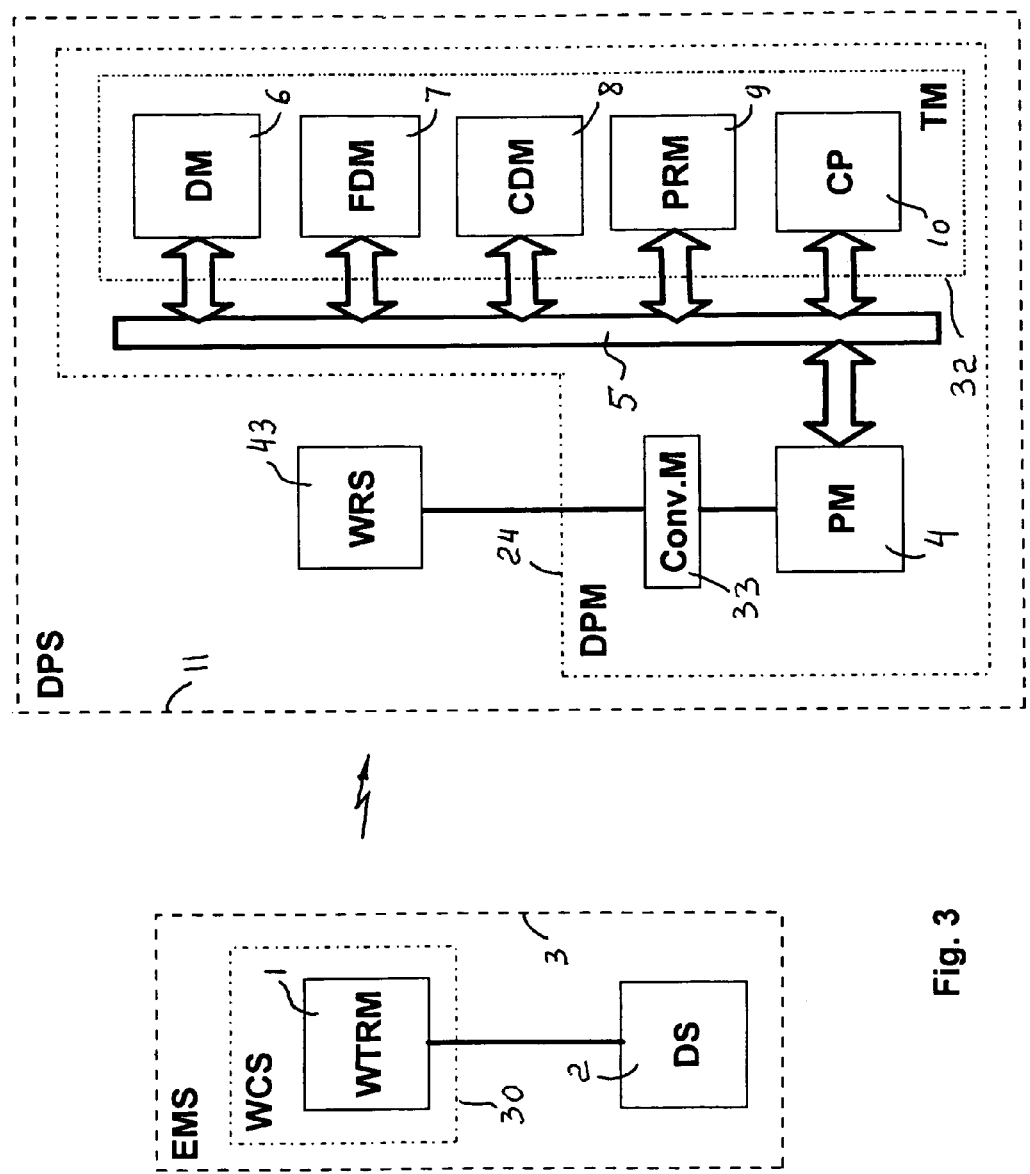
FIG. 3 is a simplified second functional block diagram of the first wireless communication variant.

FIGS. 2, 3 present the functional (detailed) block-diagram of the wireless communicating apparatus, comprising a environment monitoring system (analyzer) 3, which includes a detecting system 2 and a wireless communication system 30, including a wireless transmitting-receiving means 1. The wireless transmitting-receiving means 1 is connected to a detecting system 2.

The data processing system 11 includes a wireless receiving system 43 and data processing means 24, comprising a processing means 4, a conversion means 33 and terminal means 32. The wireless receiving system 43 is connected to the conversion means 33 of the data processing means 24. The terminal means 32 can include a displaying means 6, a floppy disk means 7, a compact disk means 8, a printing means 9 and a control panel 10 (for example, a keyboard), which are connected to each other, to the processing means 4. The connection can be provided by a multiplexed bus 5, as shown in FIGS. 2, 3. In FIG. 2, it is, as example, shown the connection of the conversion means 33 to the processing means 4 via the multiplexed bus 5, but in FIG. 3 is shown the direct connection of the conversion means 33 to the processing means 4, as the another example of their possible connection. The conversion means 33 is conventionally (conditionally) shown as a part of the data processing means 4, but the conversion means 33 can be included (not shown) in the wireless receiving system 43. The multiplexed bus 5 can be presented by a data bus and an address bus, which are not shown.

Figure 4:
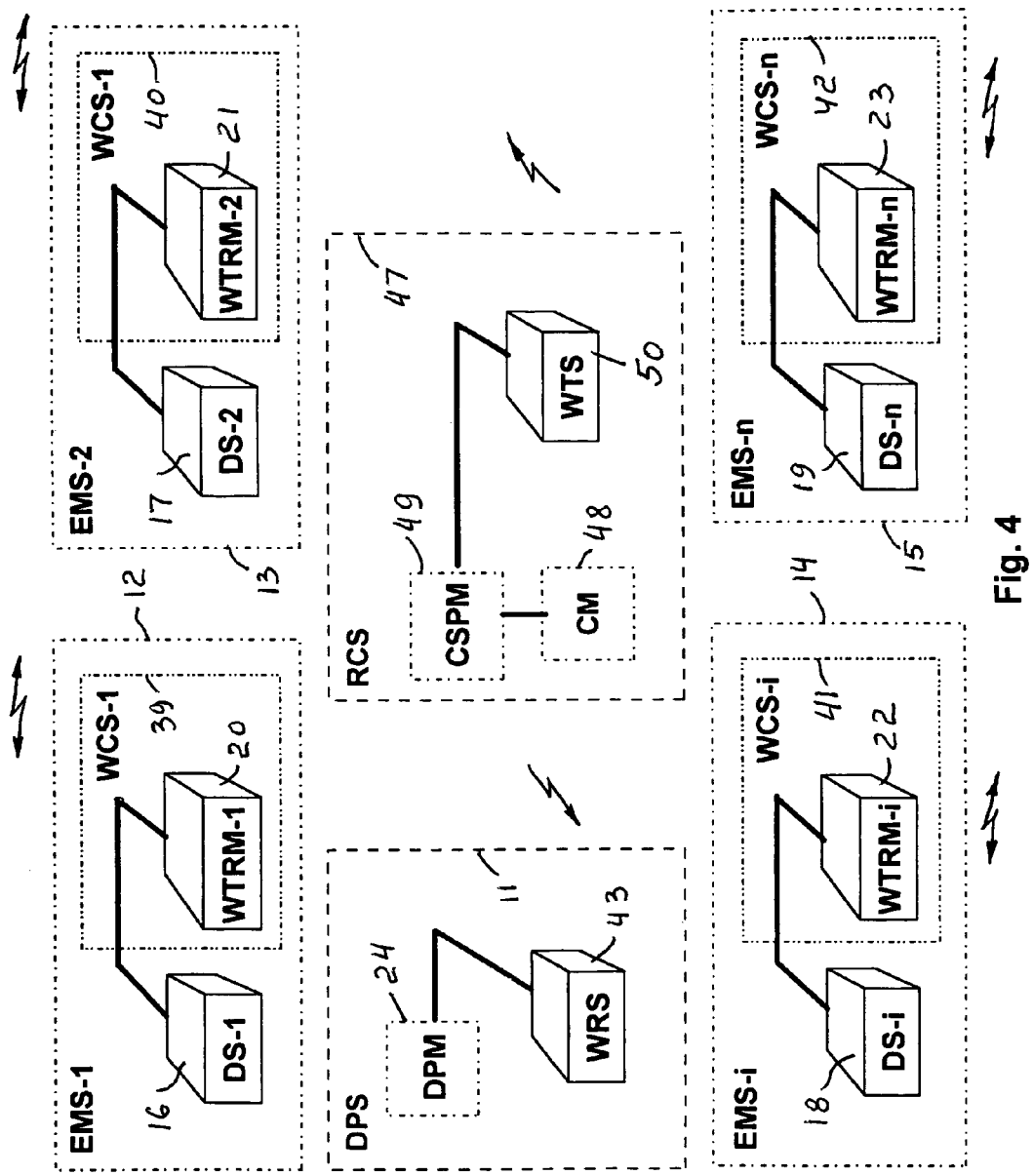
FIG. 4 is a simplified first structural block diagram of an improved wireless communicating apparatus for analysis of environment.

In FIGS. 1-3, 5-7 it is conventionally for simplification shown the communication between single data processing system 11 and single environment monitoring system 3 controlled by a single remote control system 47, but the improved wireless communicating apparatus includes at least one of a plurality of data processing systems communicating with at least one of a plurality of environment monitoring systems, as shown in FIG. 4. The communication between appropriate systems can be controlled by at least one of a plurality of remote control systems. In FIG. 4, the plurality of data processing systems and the plurality of remote control systems are conventionally presented by a single data processing system 11 and a single remote control system 47 respectively, and a plurality of environment monitoring systems is presented by 'N' (where N=1, 2, . . . , i, . . . , n) environment monitoring systems 12-15: a first environment monitoring system 12 (EMS-1), a second environment monitoring system 13 (EMS-2), an i-th environment monitoring system 14 (EMS-i) and a n-th environment monitoring system 15 (EMS-n). The first environment monitoring system 12 includes a wireless communication system 39 comprising a transmitting-receiving means 20, and a detecting system 16 connected to the transmitting-receiving means 20. The second environment monitoring system 13 includes a wireless communication system 40 comprising a transmitting-receiving means 21, and a detecting system 17 connected to a transmitting-receiving means 21. The i-th environment monitoring system 14 comprises a wireless communication system 41, including a transmitting-receiving means 22, and a detecting system 18 connected to the transmitting-receiving means 22. The n-th environment monitoring system 15 includes a wireless communication system 42 comprising a transmitting-receiving means 23, and a detecting system 19 connected to the transmitting-receiving means 23.

The data processing system 11 includes the data processing means 24 and the wireless receiving system 43. The remote control system 47 comprises the control means 48, control signal processing means 49 and the wireless transmitting system 50.

As it is mentioned above, the communication of the at least one of the plurality of environment monitoring systems with each data processing systems (if apparatus includes more than one data processing systems) can be controlled by at least one of a plurality of remote control systems 47. Each environment monitoring system can be controlled by its own remote control system (for example, the remote control system can be some kind of the TV remote control-style or some radio remote control-style, etc.), but each environment monitoring system can be controlled by more than one remote control systems if necessary, or each remote control system can control more than one environment monitoring system. In FIG. 4 is conditionally shown a single remote control system 47 controlling all environment monitoring systems (e.g. 12-15).

Finalizing the first improved variant of the analysis of environment, for example, the analysis of the air quality (i.e. detecting, counting and measuring airborne particles in the air) the method can comprise the following major steps of forming in a remote control system at least one control signal of a plurality of control signals, which provide at least a turning-on, turning-off and switching of modes of operation of said environment monitoring system (e.g. switching "run/stop", selecting and changing the particle counting and measuring channels (e.g. particle size channels, etc.), providing the remote sensor diagnostics, switching the mode (regime) from particle counting and measuring to concentration determination, selecting and changing the modes for the particle flow velocity, environmental temperature and/or humidity determination, etc.); conversing said control signals to the form for wireless transmission; wireless transmitting of the conversed control signals from said remote control system to said environment monitoring system providing the monitoring of said environment; wireless receiving of the transmitted control signals by said environment monitoring system; conversing the received control signals to the form for control of said environment monitoring system; sensing by a light detecting means of a detecting means of said environment monitoring system a light created by an intersection of said light beam with said particles within a particle monitoring region and providing an output, which is effectively indicative of a size of said particles; processing said output by a signal and data processing and control system of said environment monitoring system; forming in said signal and data processing and control system of said environment monitoring system a data, containing an information about at least one of a plurality of characteristics of the environment (e.g. about said size of said particles or said size and a quantity of said particles); conversing said data, containing said information about said size or said size and said quantity of said particles to the form for wireless transmission; wireless transmitting of the conversed data, containing said information about said size or said size and said quantity of said particles, from said environment monitoring system to said data processing system; wireless receiving of the transmitted data, containing said information about said size or said size and said quantity, by said data processing system; conversing the received data, containing said information about said size or said size and said quantity of said particles to the form for processing; processing the conversed data, containing said information about said size or said size and said quantity of said particles, by said data processing system.

Figure 5:
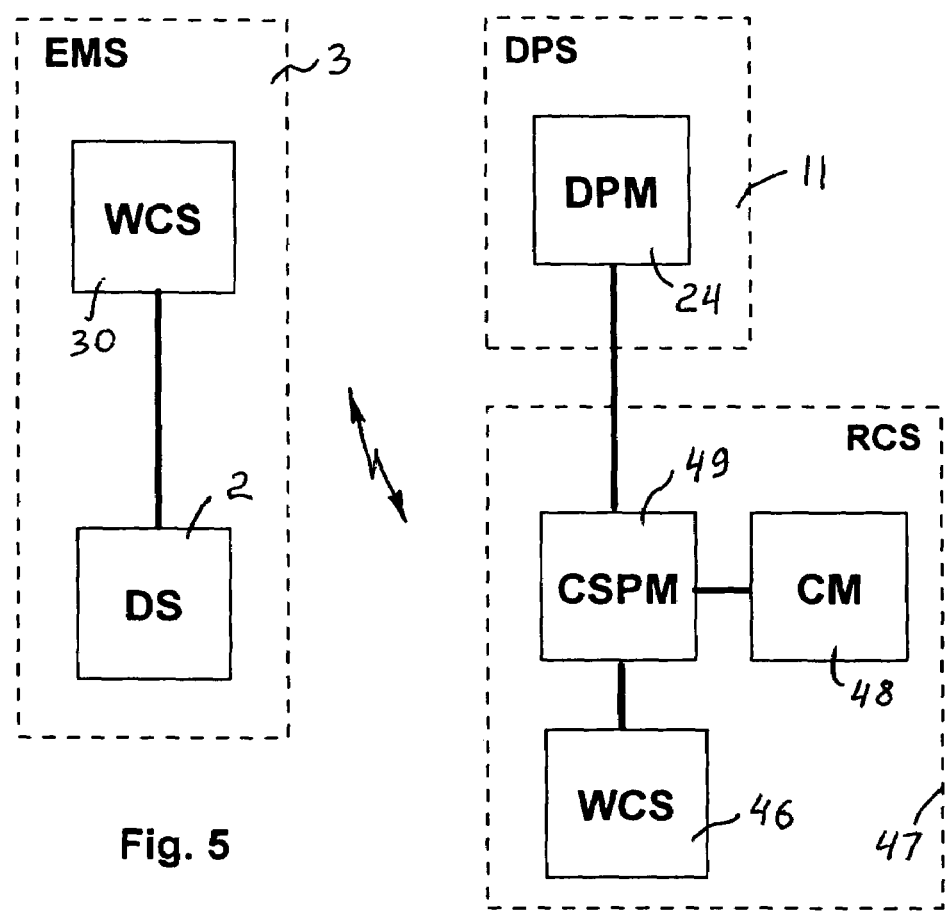
FIG. 5 is a simplified structural block diagram presentation of the second wireless communication variant.

The second variant of the wireless communication is shown in FIGS. 5-8. Referring to FIG. 5, the data processing system 11 provides only processing of the data and does not include the wireless receiving system 43 (see FIGS. 1-3). Therefore, the wireless communication of the data processing system 11 with the environment monitoring system 3 is provided only via the remote control system 47 comprising wireless communication system 46 instead of wireless transmitting system 50, and the received data follows from the wireless communication system 46 via control signal processing means 49 to the data processing means 24 of the data processing system 11. The control signal(s), controlling environment monitoring system 3 activity, follow from the control means 48 via control signal processing means 49 to the wireless communication system 46 for transmission to the environment monitoring system 3. The wireless communication system 46 can be identical with the wireless communication system 30 of the environment monitoring system(s), shown in FIGS. 1-3, 6a, 7.

Figure 6A:
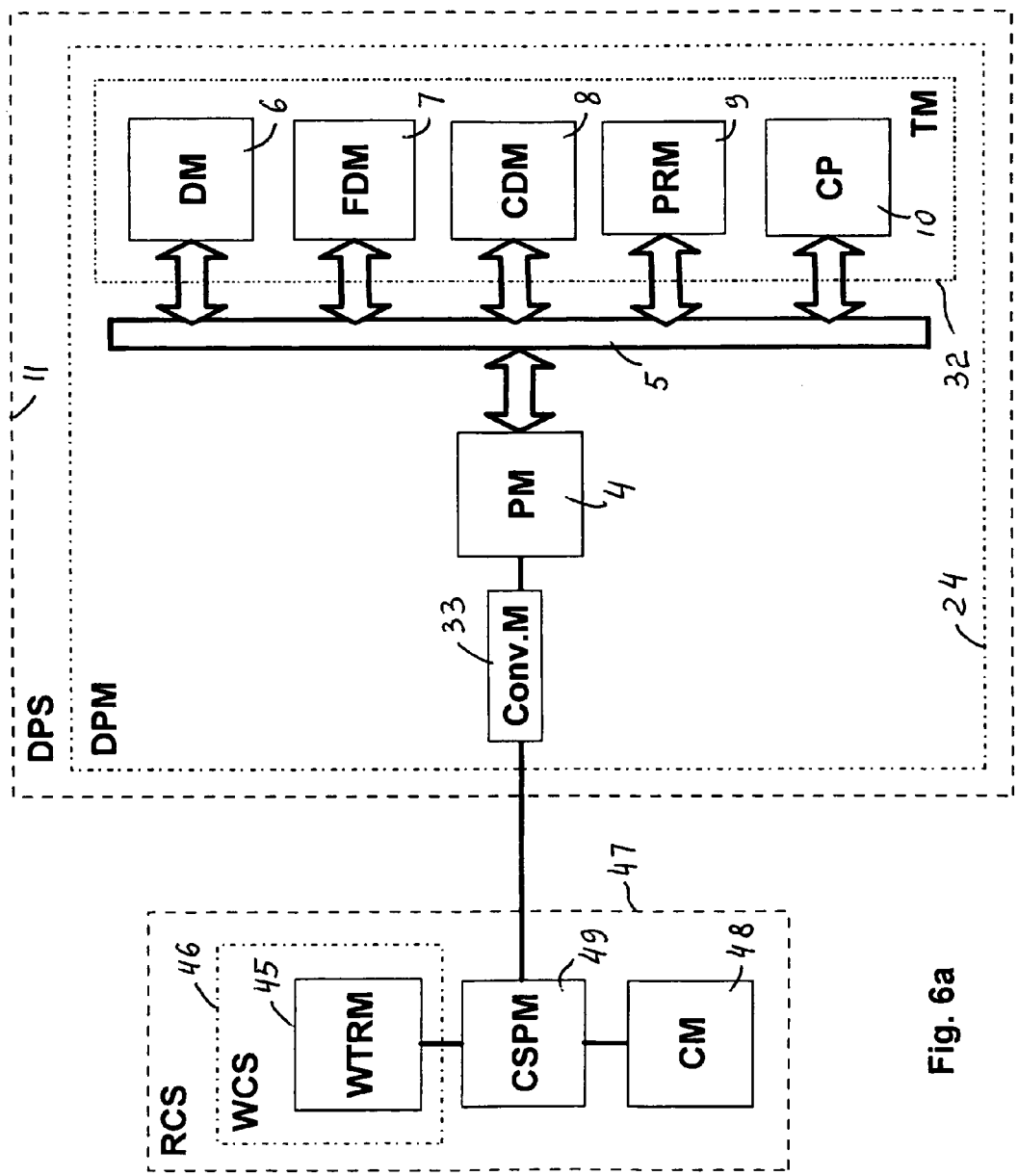
FIGS. 6a, 6b are the simplified first functional block diagrams of the second wireless communication variant.
Figure 6B:
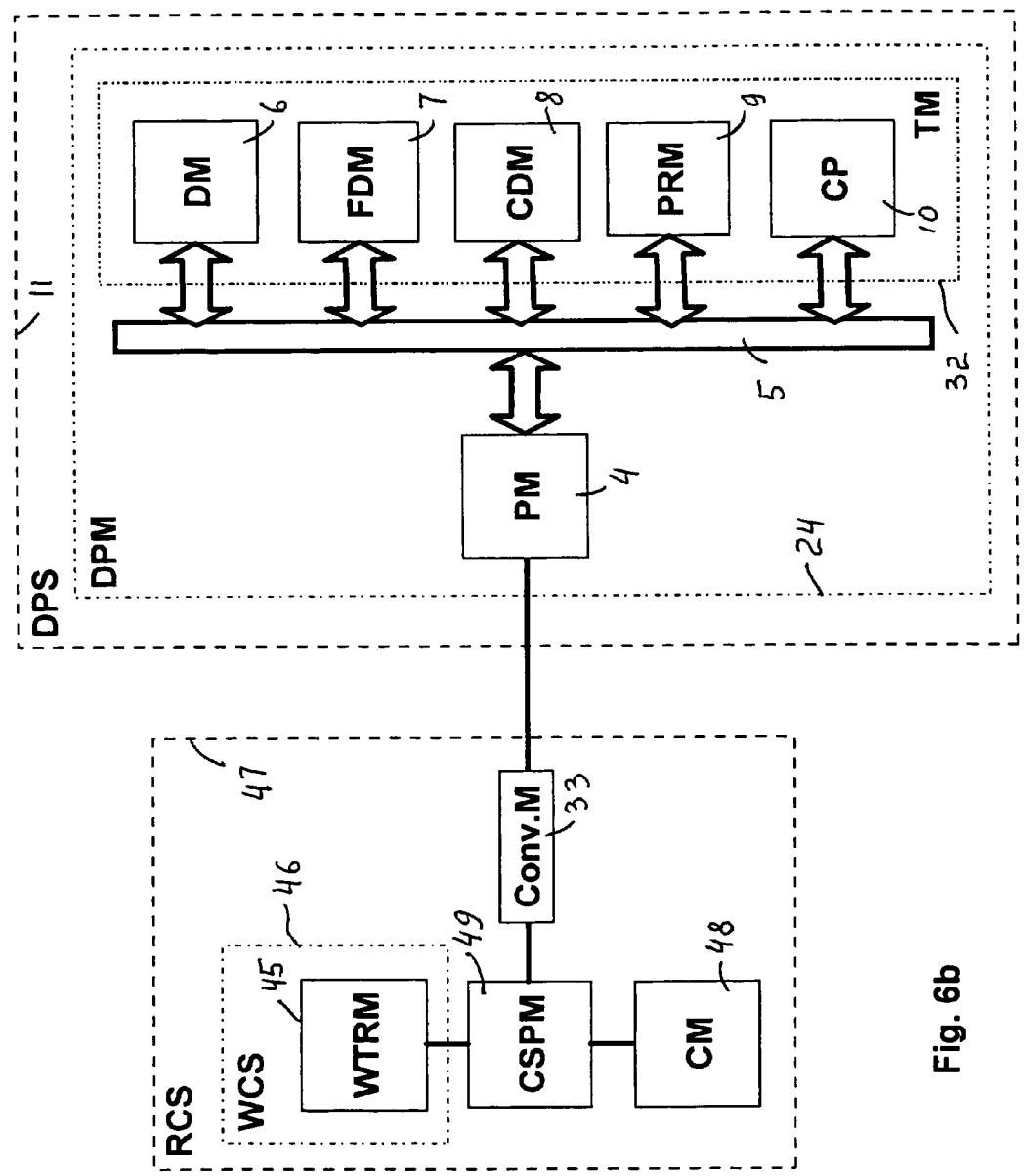
Figure 7:
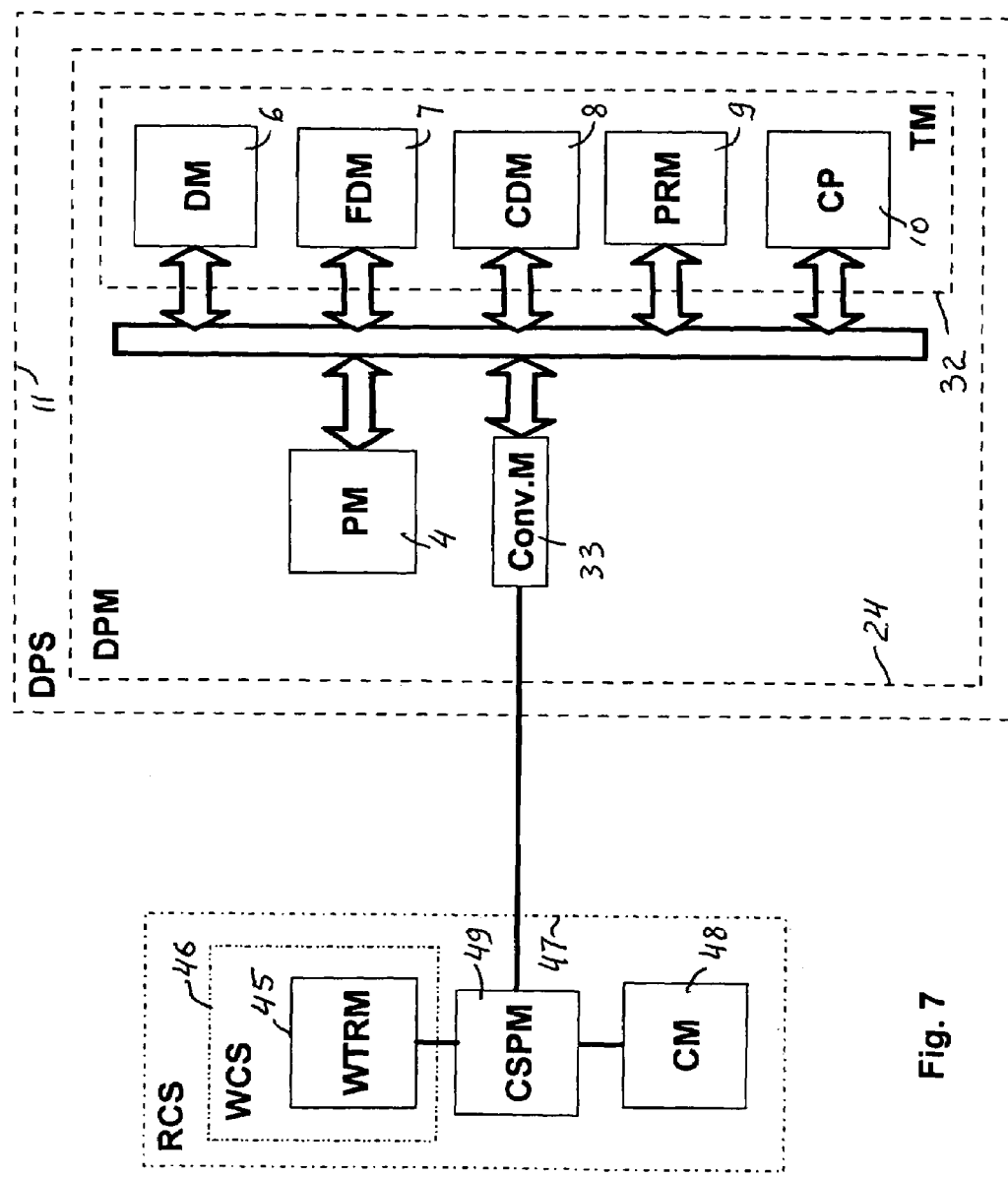
FIG. 7 is a simplified second functional block diagram of the second wireless communication variant.

FIGS. 6a, 7 show the functional (more specific, more detailed) block-diagram of the data processing 11 and remote control 47 systems. The data processing system 11 in compliance with FIG. 5 comprises a data processing means 24, including a processing means 4, a terminal means 32 and a conversion means 33. The conversion means 33 is connected to the processing means 4, which is connected by a multiplexed bus 5, as shown in FIG. 6a, to the terminal means 32 including at least one of a displaying means 6, a floppy disk means 7, a compact disk means 8, a printing means 9 and a control panel 10 (for example, a keyboard), which are connected to each other by the same bus 5. The conversion means 33 can be connected to the processing means 4 via the multiplexed bus 5, as it is shown in FIG. 7. The multiplexed bus 5 can be also presented by a data bus and an address bus, which are not shown. Any and/or all systems, means and components of the improved apparatus can communicate to each other by any reasonable type of communications and any and/or all connection presented in the improved environmental analyzer can be of any reasonable king including cordless/wireless (not shown), for instance, humidity, temperature sensors and others (not shown) can communicate wirelessly too. The control signal processing means 49 of the remote control system 47 is connected to control means 48, wireless communication system 46, and the conversion means 33 of the data processing system 11. The wireless communication system 46 includes a transmitting-receiving means 45. The conversion means 33 is conventionally (conditionally) as example shown in FIGS. 6a, 7 as a part of the data processing means 4, but the conversion means 33 can be included in the remote control system 47, as it is as example shown in FIG. 6b.

Figure 8:
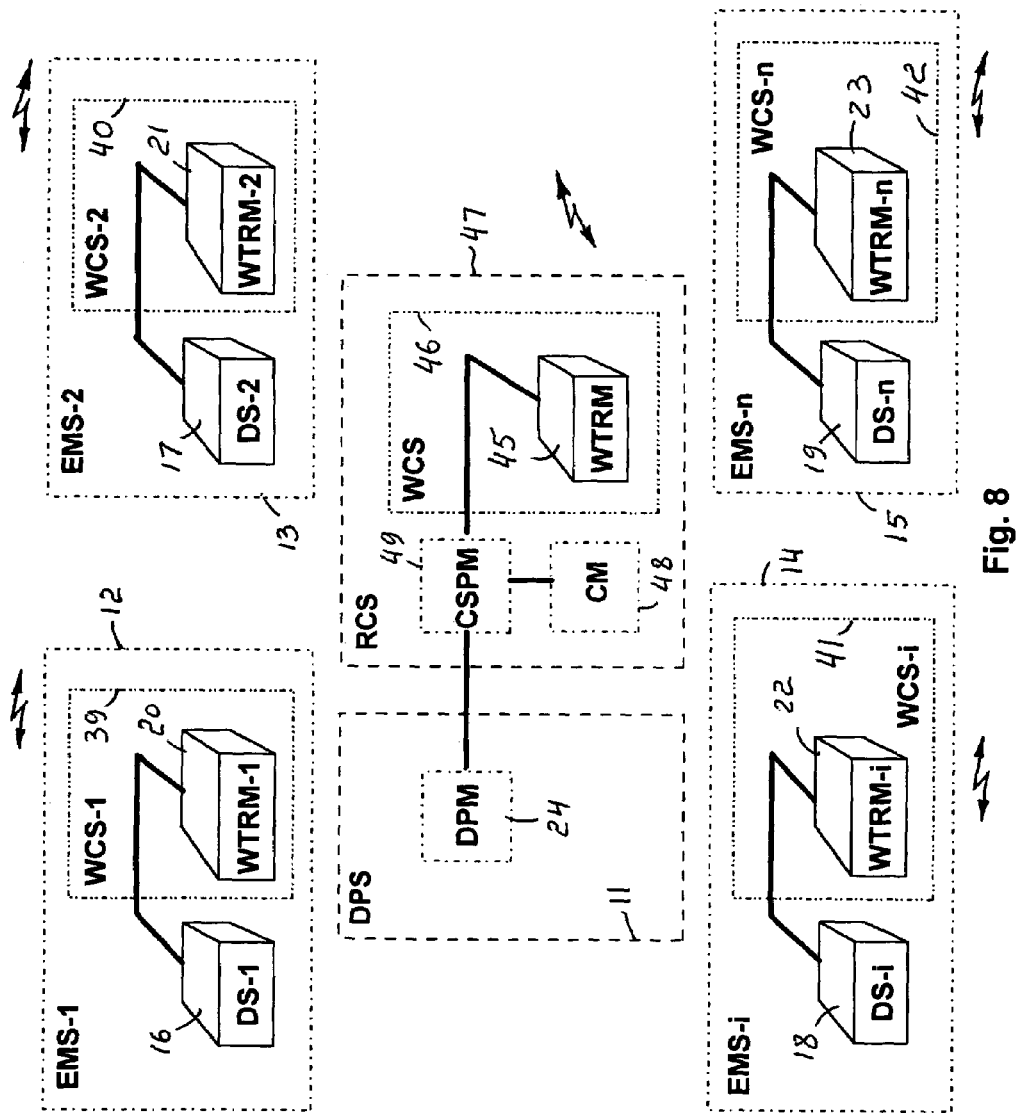
FIG. 8 is a simplified second structural block diagram of an improved wireless communicating apparatus for analysis of environment.

FIG. 8 illustrates the improved wireless communicating environmental analyzer. The plurality of data processing systems and the plurality of remote control systems are conventionally presented by a single data processing system 11 and a single remote control system 47 respectively, and the plurality of environment monitoring systems is respectively presented by "N" (where N=1, 2, . . . , i, . . . , n) environment monitoring systems 12-15: a first environment monitoring system 12 (EMS-1), a second environment monitoring system 13 (EMS-2), an i-th environment monitoring system 14 (EMS-i) and a n-th environment monitoring system 15 (EMS-n). The first environment monitoring system 12 includes a wireless communication system 39 comprising a transmitting-receiving means 20, and a detecting system 16 connected to the transmitting-receiving means 20. The second environment monitoring system 13 includes a wireless communication system 40 comprising a transmitting-receiving means 21, and a detecting system 17 connected to a transmitting-receiving means 21. The i-th environment monitoring system 14 comprises a wireless communication system 41, including a transmitting-receiving means 22, and a detecting system 18 connected to the transmitting-receiving means 22. The n-th environment monitoring system 15 includes a wireless communication system 42 comprising a transmitting-receiving means 23, and a detecting system 19 connected to the transmitting-receiving means 23.

The data processing system 11 includes the data processing means 24. The remote control system 47 comprises the control means 48, control signal processing means 49 and the wireless communication system 46 including wireless transmitting-receiving means 45.

Additionally, as it was describe above for apparatus shown in FIG. 4, the communication of each data processing systems (if apparatus includes more than one data processing systems) with the at least one of the plurality of environment monitoring systems can be controlled by at least one of a plurality of remote control systems, but each remote control system can control more than one data processing system and more than one environment monitoring system, or each environment monitoring system can be controlled by its own remote control system etc., as it is described above regarding apparatus shown in FIG. 4.

Finalizing the second improved variant of the analysis of environment, for example, the analysis of the air quality (i.e. detecting, counting and measuring airborne particles in the air) the method can comprise the following major steps of: forming in a remote control system at least one control signal of a plurality of control signals, which provide at least a turning-on, turning-off and switching of modes of operation of said environment monitoring system (e.g. switching "run/stop", selecting and changing the particle counting and measuring channels (e.g. particle size channels, etc.), providing the remote sensor diagnostics, switching the mode (regime) from particle counting and measuring to concentration determination, selecting and changing the modes for the particle flow velocity, environmental temperature and/or humidity determination, etc.); conversing said control signals to the form for wireless transmission; wireless transmitting of the conversed control signals from said remote control system to said environment monitoring system providing the monitoring of said environment; wireless receiving of the transmitted control signals by said environment monitoring system; conversing the received control signals to the form for control of said environment monitoring system; sensing by a light detecting means of a detecting means of said environment monitoring system a light created by an intersection of said light beam with said particles within a particle monitoring region and providing an output, which is effectively indicative of a size of said particles; processing said output by a signal and data processing and control system of said environment monitoring system; forming in said signal and data processing and control system of said environment monitoring system a data, containing an information about said size of said particles or said size and a quantity of said particles; conversing said data, containing said information about said size or said size and said quantity of said particles to the form for wireless transmission; wireless transmitting of the conversed data, containing said information about said size or said size and said quantity of said particles, from said environment monitoring system to said remote control system; wireless receiving of the transmitted data, containing said information about said size or said size and said quantity of said particles, by remote control system; transferring the received data, containing said information about said size or said size and said quantity of said particles, to said data processing system; conversing the transferred data, containing said information about said size or said size and said quantity of said particles, to the form for processing; processing the conversed data, containing said information about said size or said size and said quantity of said particles, by said data processing system.

The data processing system(s) and/or remote control system(s) can be stationary or portable. The communication between environment monitoring system and remote control system, between environment monitoring system and data processing system and remote control system, and between data processing system and remote control system can be provided in compliance with any reasonable principles including regular wire connection or wireless (cordless) one-way and/or two-way communications, etc.

Figure 9:
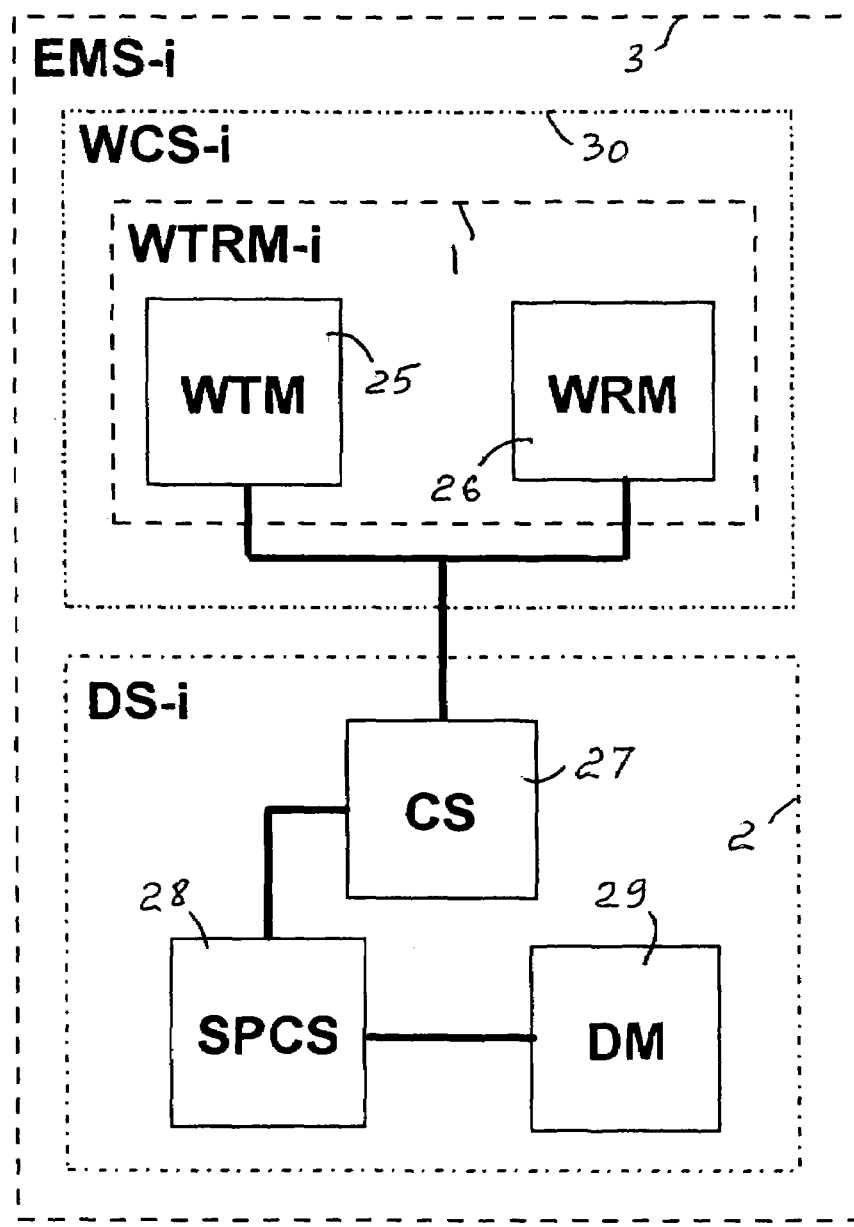
FIG. 9 is a simplified structural block diagram of the environment monitoring system of an improved apparatus.

FIG. 9 illustrates the environment monitoring system 3 shown in FIGS. 1-3, 5-7 or the environment monitoring systems 12-15 shown in FIGS. 4, 8. The environment monitoring system 3 and systems 12-15 can be identical. Each environment monitoring system (at least one of a plurality of the environment monitoring systems "N") can include a detecting system 2, comprising a detecting means 29 connected to a signal processing and control system 28 (hereinafter a signal processing and control system can be mentioned as a processing and control system), which is connected to a conversion system 27. Also, each environment monitoring system (in FIG. 9 it is conditionally shown number 3) comprises a wireless communication system (e.g. 30, 39-42 respectively, and in FIG. 9 it is conditionally shown number 30) including the appropriate transmitting-receiving means (e.g. 1, 20-23 respectively, and in FIG. 9 it is conditionally shown number 1) each comprising an appropriate transmitting means 25 and receiving means 26, which are connected to the conversion system 27.

Figure 10:
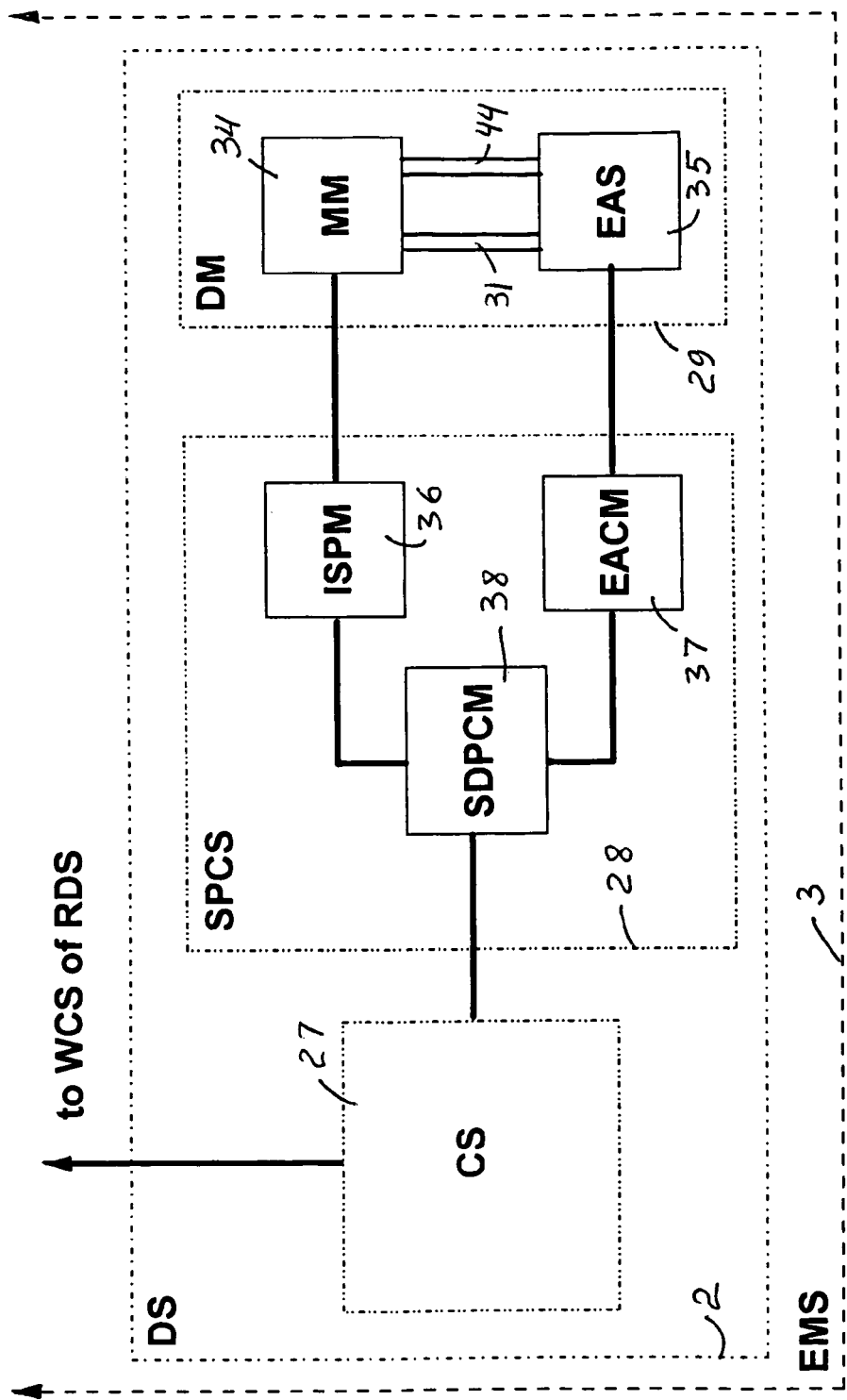
FIG. 10 is a simplified functional block diagram of the detecting system of an improved environment monitoring system.

FIG. 10 illustrates the detecting system 2, which comprises a conversion system 27, which can include some signal and data conversing means (not shown), some coding-decoding means (not shown), etc. The appropriate systems and means of the detecting system can be connected either by a multiplexed bus (not shown) or by regular connection (not shown). The data bus and address bus (both not shown) can be used instead of the multiplexed bus. Also, the detecting system 2 comprises a signal processing and control system 28 and a detecting means 29. The signal processing and control system 28 includes a initial signal processing means 36 connected to a signal and data processing and control means 38, which is connected to the conversion system 27 and to environment assaying control means 37.

The detecting means 29 includes a monitoring means 34, connected to the initial signal processing means 36 of the signal processing and control system 28. The monitoring means 34, providing, for example, the sensing (detection) of the airborne particles in the assayed air for further their measuring and counting, can include the light detecting system/means (partially shown in FIG. 16) and optical/mirror system/means (also partially shown in FIG. 16). The detecting means 29 also includes an environment assaying system 35, which is connected to the environment assaying control means 37 of the signal processing and control system 28, and which is coupled with the monitoring means 34 by the capillary inlet flow means 31 and capillary outlet flow means 44. The environment assaying control means 37 may be included (not shown) in the signal and data processing and control means 38 or may be included (not shown) in the environment assaying system 35.

Figure 11:
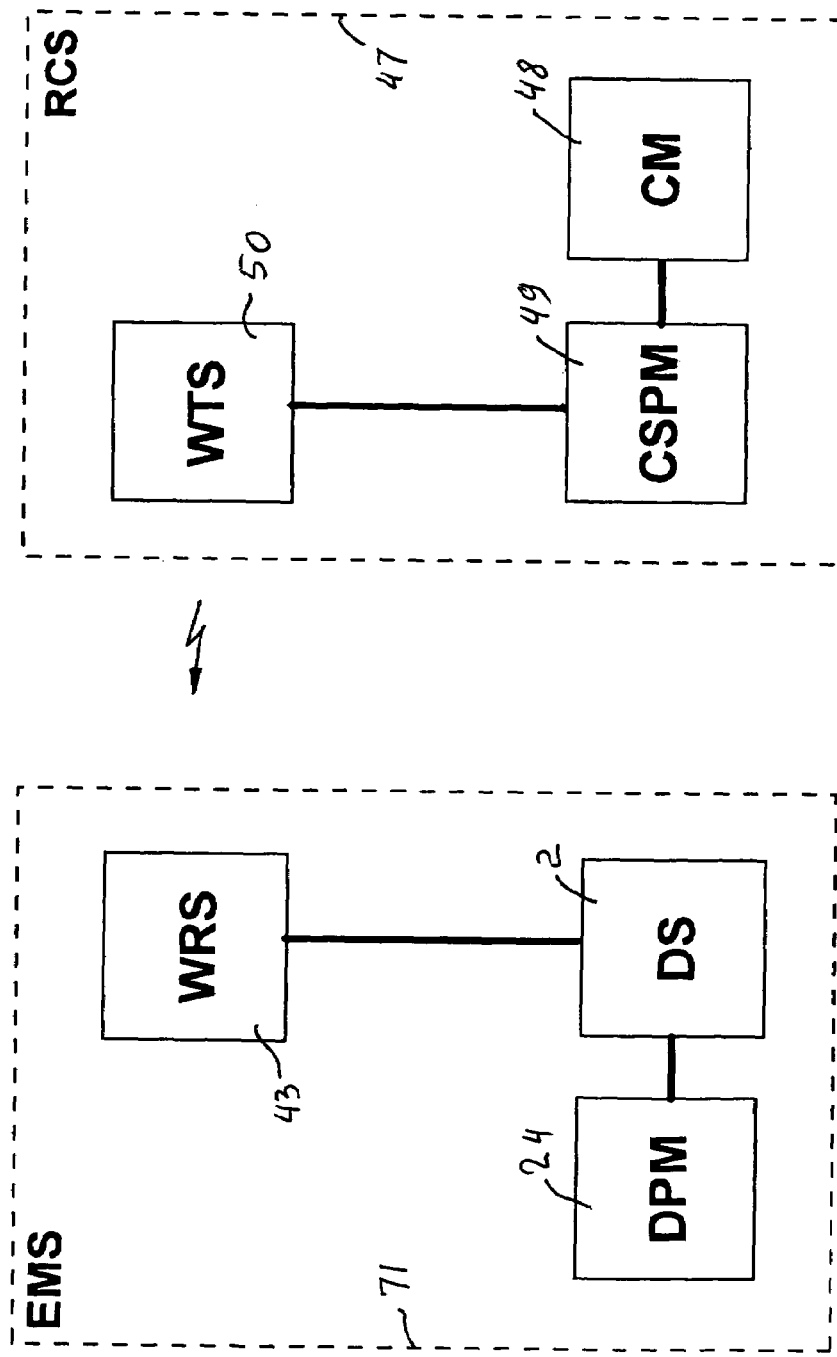
FIG. 11 is a simplified structural block diagram presentation of the third wireless communication variant.
Figure 12:
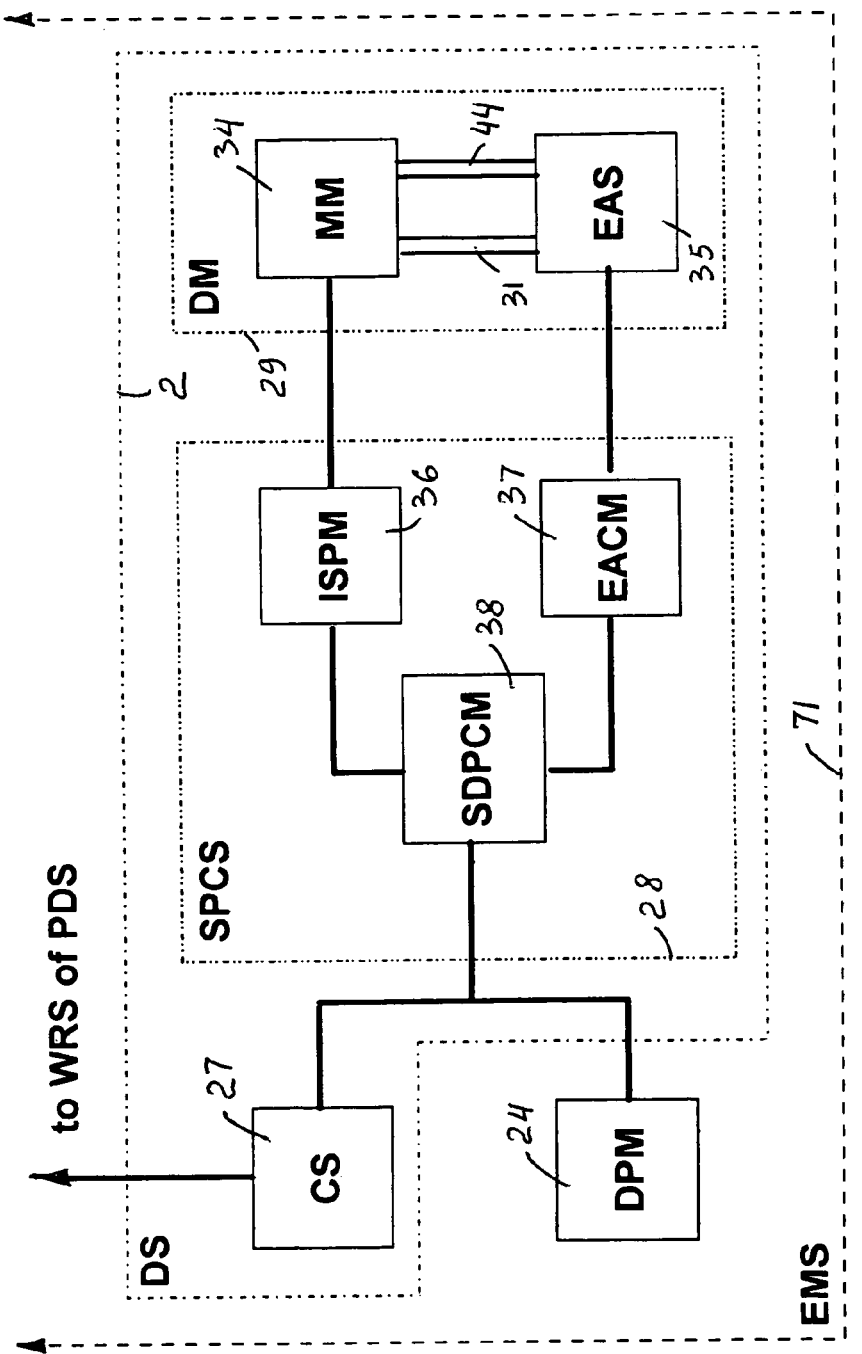
FIG. 12 is a simplified functional block diagram of the detecting system using the third wireless communication variant.

Referring to FIG. 11, the improved apparatus includes a remote control system 47 and an environment monitoring system 71, which can comprise the detecting system 2, data processing means 24, and wireless receiving system 43. The data processing means 24 is connected to the signal and data processing and control means 38, as shown in FIG. 12.

Figure 13:
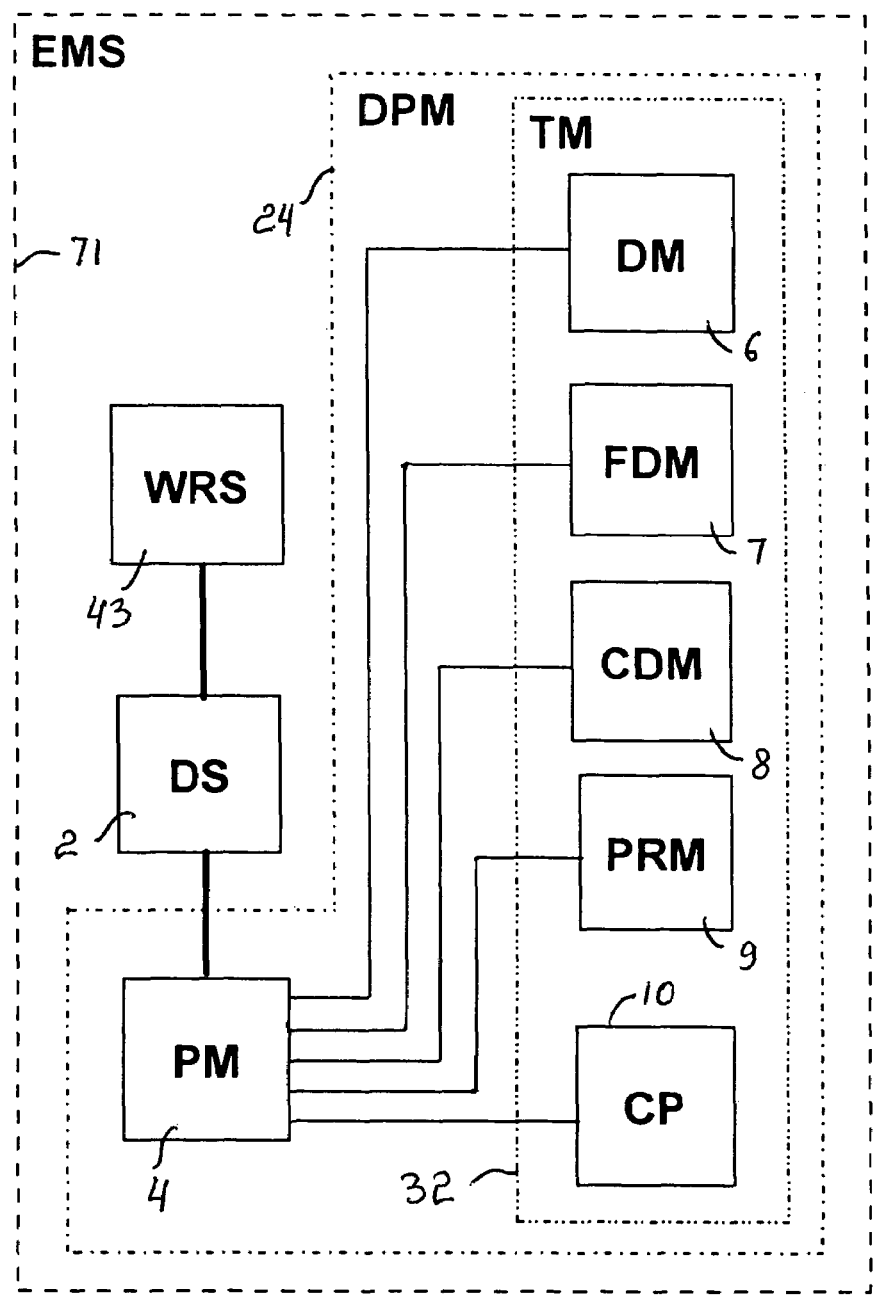
FIGS. 13, 14 are the structural block diagrams of the environment monitoring system using the third wireless communication variant.
Figure 14:
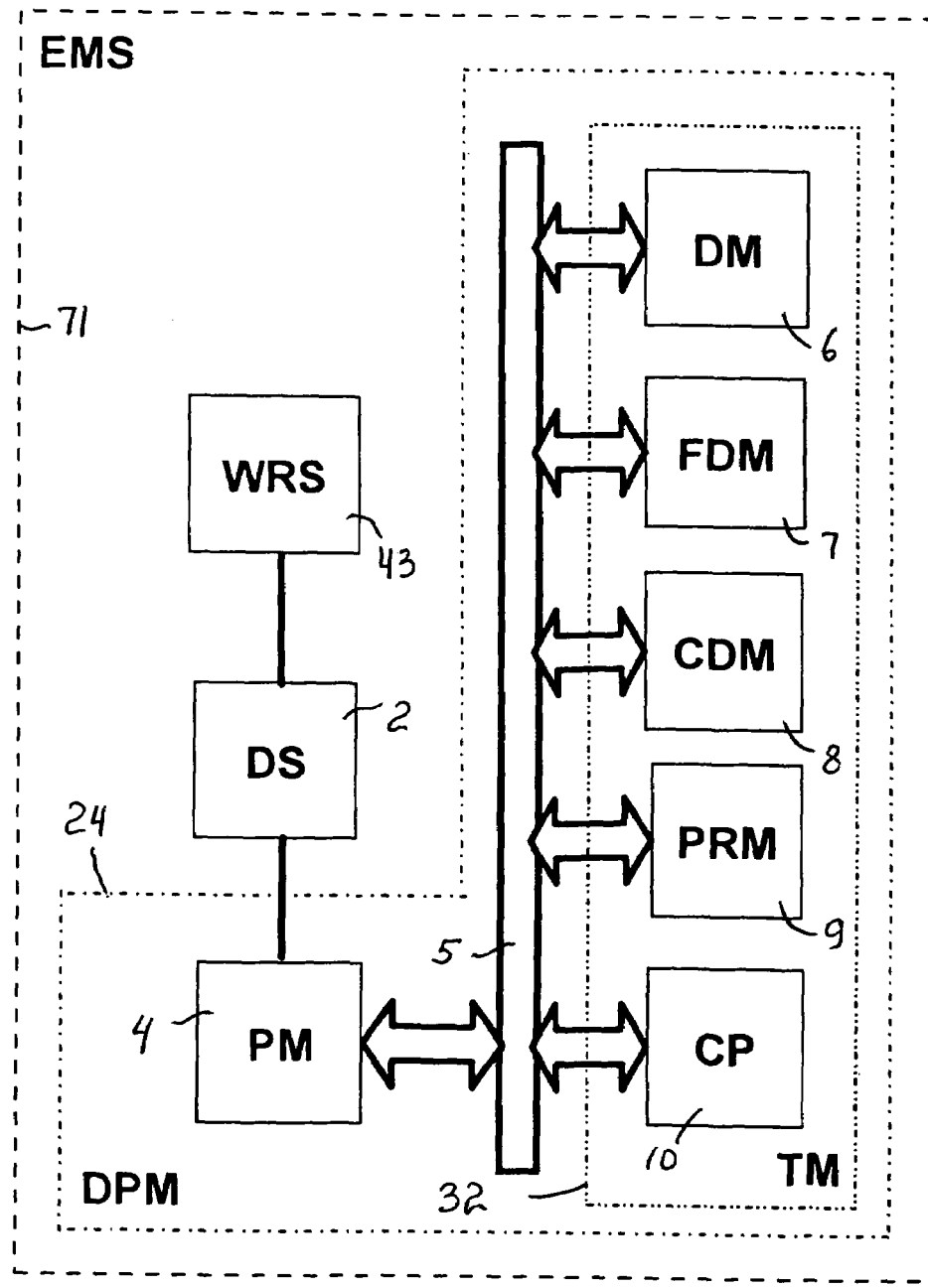

FIGS. 13, 14 illustrate the wireless communicating (wireless controlled) environment monitoring system 71. The data processing means 24 comprising the terminal means 32, which can include at least one of the displaying means 6, printing means 9, front control panel 10 (and possibly the floppy disk means 7 and/or compact disk means 8) connected to the processing means 4, as shown in FIG. 13. According to FIG. 14, the described connection can be provided by the multiplexed bus 5 (the data bus and address bus can be used to /both not shown/). The signal and data processing and control means 38 (see FIG. 12) of the portable environment monitoring system 71 can perform (not shown) the functions of the data processing means 24, thereby eliminating necessity of the data processing means 24 presence in the environment monitoring system. According to this matter, the environment monitoring system 71 will be presented by the environment monitoring system 5, the signal and data processing and control means 38, which additionally performs (not shown) the functions of the eliminated data processing means 24.

Finalizing the third improved variant of the analysis of environment, for example, the analysis of the air quality (i.e. detecting, counting and measuring airborne particles in the air) the method can comprise the following major steps of: forming in a remote control system at least one control signal of a plurality of control signals, which provide at least a turning-on, turning-off and/or switching of modes of operation of said environment monitoring system (e.g. switching "run/stop", selecting and changing the particle counting and measuring channels (e.g. particle size channels, etc.), providing the remote sensor diagnostics, switching the mode (regime) from particle counting and measuring to concentration determination, selecting and changing the modes for the particle flow velocity, environmental temperature and/or humidity determination, etc.); conversing said control signals to the form for wireless transmission; wireless transmitting of the conversed control signals from said remote control system to said environment monitoring system; wireless receiving of the transmitted control signals by said environment monitoring system; conversing the received control signals to the form for control of said environment monitoring system; sensing by a light detecting means of a detecting means of said environment monitoring system a light created by an intersection of said light beam with said particles within a particle monitoring region and providing an output, which is effectively indicative of a size of said particles; processing said output by a signal and data processing and control system of said environment monitoring system; forming in said signal and data processing and control system of said environment monitoring system a data, containing an information about said size of said particles or said size and a quantity of said particles; displaying or printing said information about said size of said particles or said size and a quantity of said particles.

Figure 15:
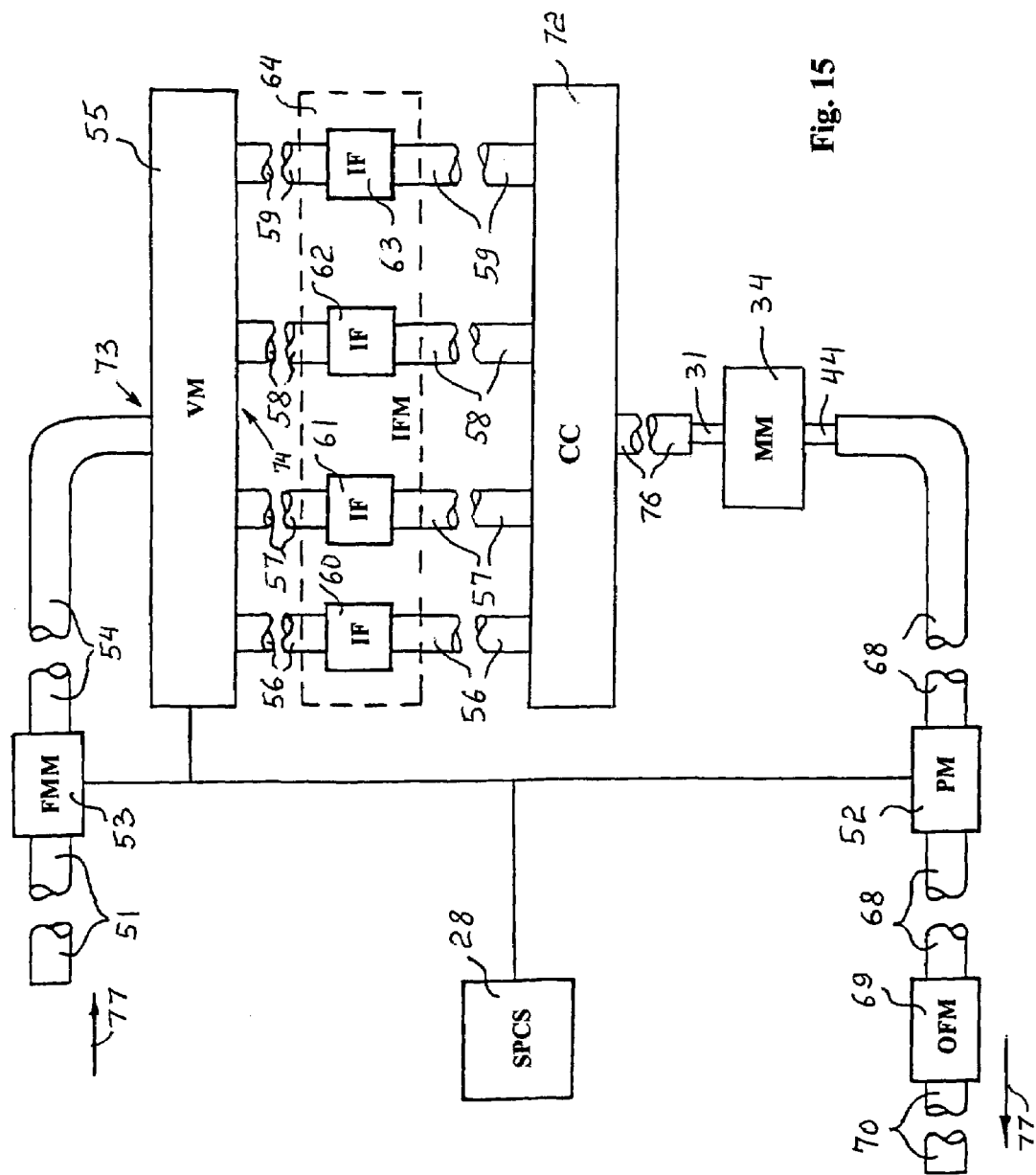
FIG. 15 is a structural kinematic diagram of the assayed specimen flow.
Figure 16:
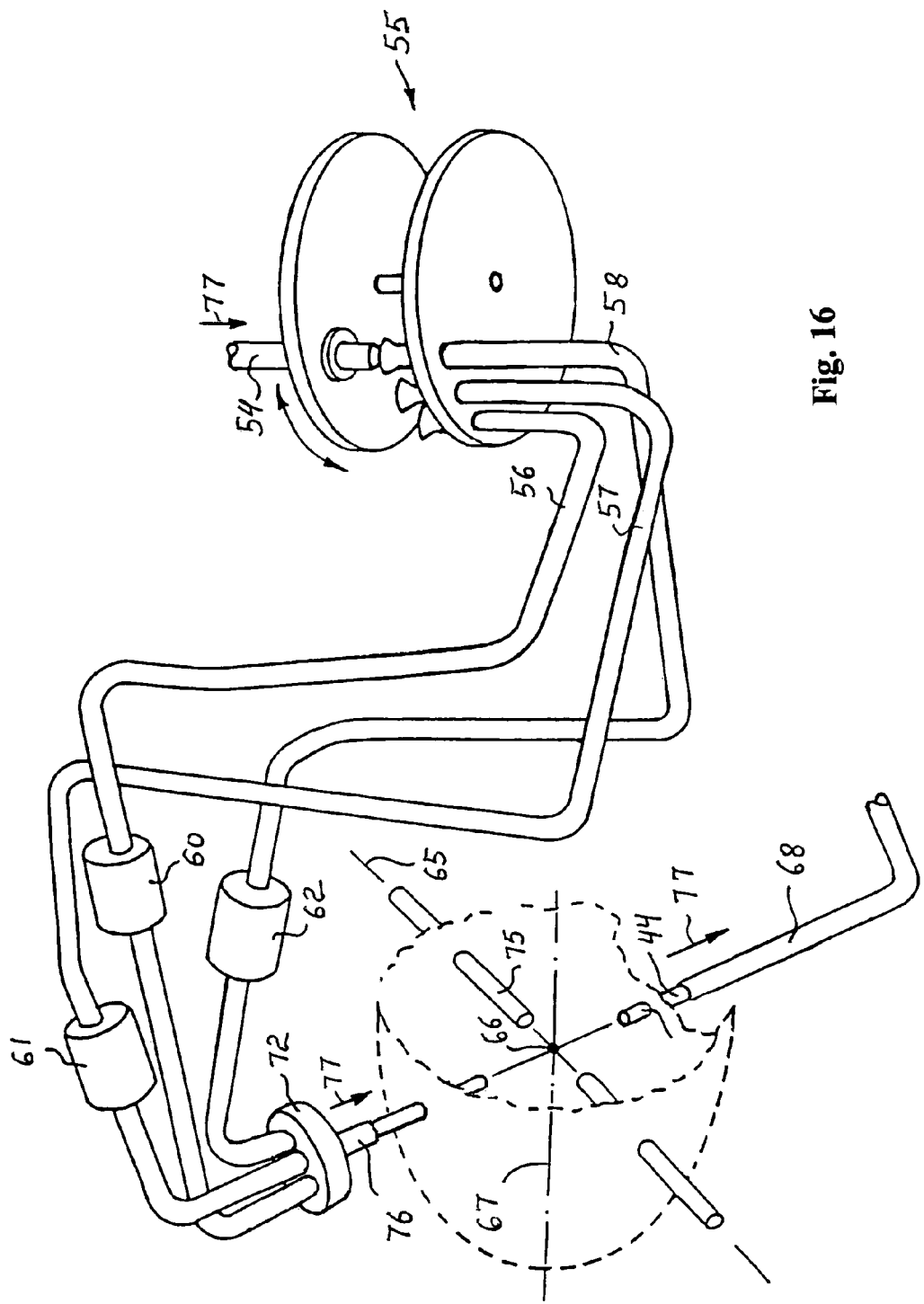
FIG. 16 is a simplified drawing of the certain aspects of the tubular means coupling.

FIG. 15 shows the structural kinematic diagram of the assayed specimen flow and FIG. 16 illustrates the certain aspects of the environment assaying system 35 (see also FIG. 10). The improved environment assaying system operate as follow below. Referring to FIG. 15, the outside of the analyzer 3 environment (for example, an air for particle counting and measuring, but it could be gas, liquid/water, etc.) assayed by the pumping means 52 from the entrance flow tubular means 51 through the flow measuring means 53 by an extended entrance particle flow tubular means 54 flows in derection 77 to the inlet portion 73 of the valving means 55. The valving means 55 can be of any reasonable design (for instance, non-controllable or controllable /e.g. manually or automatically, etc./), form, configuration, size and color, etc., for example, the valving means 55 can be of in-line channel design (not shown) or rotary design, as show in FIG. 16. The pumping means 52 can be presented by any reasonable means providing assayed specimen flow through the monitoring means 34 of the detecting means 29 of the environment monitoring system 3. For instance, the pump(s), centrifugal blower(s) and/or any purging means, etc. can be used for specimen assaying. The operation of the pumping means 52 and flow measuring means 53 can be controllable, as it is shown in FIG. 15, or non-controllable (not shown). The control of the pumping means 52 and/or flow measuring means 53 can be provided by the signal processing and control system 28 (see FIG. 15).

The controllable valving means 55 distributes from its outlet portion 74 the air flow (particle flow) to one of M=1, 2, . . . , j, . . . , m particle flow channels, depending on the particle size, which is intended for the counting and measuring. For example, assume that the intended channel will be the j-th channel (in FIG. 15 conditionally shown four flow channel: the first channel is provided by an extended inlet particle flow tubular means 56, second channel is provided by an extended inlet particle flow tubular means 57, j-th channel is provided by an extended inlet particle flow tubular means 58 and m-th cannel is provided by an extended inlet particle flow tubular means 59). The particles flow by the appropriate extended inlet particle flow tubular means 58 through an j-th particle flow inlet filter 62 of an inlet filtrating means 64, and through a channel connector 72 via channel connector outlet tubular means 76 and capillary inlet flow means 31 into monitoring means 34 of detecting means 29.

Each particle flow inlet filter 60-63 of the inlet filtrating means 64 is intended for one size particles only. It means, for example, if j-th channel is intended for counting and measuring 0.5 μm particles, the particle flow inlet filter 62 filtrates everything over 0.5 μm, providing a particle sorting for the further passage of already predetermined size particles through the capillary inlet flow means 31. The monitoring means 34 of the detecting system 2 (further, for instance, the particle detecting system, if the monitored characteristic is the contamination/particle size, etc.) monitors the particles in the assayed specimen flow (in the assayed /pumped in/ environment) by a light (laser) beam 75 intersecting the particle flow, and producing an output(s) (e.g. initial signal/s/) effectively indicative of the particle characteristic (e.g. particle size).

The improved method provides steps as follows below. The axis of the capillary inlet particle flow means 31 is coincident with the axis of the capillary outlet particle flow means 44 and intersects a light beam axis 65 on the device axis (optical system axis) 67 at the optic focal point 66, as it is shown in FIG. 16. It is conditionally, as example, shown the three channels and the ellipsoidal mirror system in FIG. 16, but any optical/mirror system, providing particle monitoring, can be used. By the improved method, the particles of the particle flow pass through the focal point (focus) 66. The initial signals, related to the particles, from monitoring means 34 follow to the signal processing and control system 28 for processing, forming data containing information about particle characteristic(s) (e.g. particle size and quantity). The monitored particles flow through capillary outlet particle flow means 44, extended outlet particle flow tubular means 68, pumping means 52, outlet filtrating means 69 and the exhaust particle flow tubular means 70 to the outside environment. The air flow is measured by controllable flow measuring means 53, which is also controlled by a signal processing and control system 28 or data processing means 24 of the data processing system 11 (not shown in FIG. 15), and information (e.g. processed by the signal processing and control system 28 or data processing means 24 of the data processing system 11) about air flow characteristics can be indicated by the terminal means 32 to the operator (computer operator). The temperature sensor (not shown) and/or other sensors can be in the presence too.

For monitoring of the liquids (drinking water, for example), an improved apparatus can comprise an entire undivided capillary particle flow means (not shown) instead of the capillary inlet 31 and outlet 44 flow means. All capillary flow means including mentioned solid (undivided) capillary flow means can be of any reasonable form and configuration, for example, the square or circular geometric inside/outside form with inside dimensions correlated to the largest predetermined size particle. The capillary particle flow system, as a module of the detecting system, can be interchangeable to provide the other needed environmental analysis.

The first improved variant (illustrated by FIGS. 1-4) provides a wireless communication, i.e. a wireless transmitting of the control signal(s), from the remote control system(s) (e.g. 47) to the appropriate environment monitoring system(s) (e.g. 12-15) and a wireless transmitting of the data (information), characterizing the detected (monitored) environment (e.g. particle size, quantity, etc.), from the environment monitoring system(s) to the data processing system(s) (e.g 11) directly. The second improved variant (illustrated by FIGS. 5-8) provides a wireless communication, i.e. a wireless transmitting of the control signal(s) from the remote control system(s) (e.g. 47) to the appropriate environment monitoring system(s) (e.g. 12-15) and a wireless transmitting of the data (information), characterizing the detected (monitored) environment, from a environment monitoring system(s) to the appropriate data processing system(s) (e.g 11) via the appropriate remote control system(s) (e.g. 47). The third improved variant (illustrated by FIGS. 11-14) provides a wireless communication, i.e. a wireless transmitting of the control signal(s) from remote control system(s) (e.g. 47) to the appropriate environment monitoring system(s).

An improved wireless communicating apparatus operates as follows. The wireless communicating apparatus for analyzing of environment according to (see FIGS. 1-8) can operate in the three modes: manual service of the data processing system 11 and/or remote control system 47 by the operator (e.g. computer operator), using a control panel (e.g. a computer's key board) 10 of the terminal means 32 of the data processing system 11 for computer control or for control of the environment monitoring system(s) (e.g. 12-15), and/or using the control means 48 of the remote control system 47 for communication control; automatically by a priori programmed stages, conditions, regimes and schedule of the operation, and/or recorded, for example, on the floppy disk means 7, or on the compact disk means 8 of the data processing means 24, or in programmable/reprogrammable means (not shown) of the processing means 4 for the computer control, and/or control signal processing means 49 for communication control (if, for example, the control signal processing means 49 includes its own recordable means, such as floppy disk means /not shown/, compact disk means /not shown/ or programmable/reprogrammable means /not shown/); and the third mode is the different variations of the manual and automatic modes combination.

According to the first improved variant (illustrated by FIGS. 1-4) and regarding the manual mode of the operation, the operator manually (e.g. by the control means 48) selects the regimes (mode(s), command(s), etc.) for the environment monitoring system 3 operation. The control signals from the control means 48 follow to the control signal processing means 49 of the remote control system 47. Referring to automatic mode of the operation, the regime(s) are selected and/or prerecorded either by a floppy disk means (not shown), or by compact disk means (not shown), or by programmable/reprogrammable means (not shown) of the control signal processing means 49.

The control signals (controlling the appropriate environment monitoring system(s)) processed by the control signal processing means 49 follow to the wireless communicating means (wireless transmitting system 50) of the remote control system 47 for transmitting to the selected appropriate environment monitoring system(s).

The control signal(s) can provide, for example, possibility to switch "on/off", to switch "run/stop", to select and change the particle counting and measuring channels (e.g. particle size, etc.), to provide remote sensor diagnostics, to switch the mode (regime) from particle counting and measuring to concentration determination, to select and change the modes for the particle flow velocity, environmental temperature and/or humidity determination, etc.

The control signals received by the wireless communicating system (e.g. wireless communication system 30 of the environment monitoring system 3, for example, according to FIGS. 1-3) follow from the transmitting-receiving means 30 to the detecting system 2 for environment analysis as it is mentioned above and illustrated in FIGS. 15, 16.

According to FIG. 5 illustrating the second improved variant, the wireless communication system 46 of the remote control system 47 communicates (transmits-receives) with the wireless communication system 30 of the environment monitoring system 3 (referring to FIG. 8, the wireless communication system 46 of the remote control system 47 communicates with the wireless communication systems 39-42 of the appropriate environment monitoring systems 12-15 respectively). The control signal(s) from the remote control system 47 are received by the receiving means (not shown in FIG. 5, but shown as 26 in FIG. 9) of the transmitting-receiving means (not shown in FIG. 5, but shown as 1 in FIG. 9) of the wireless communication system 30 of the environment monitoring system 3 and follow via conversion system 27 of the detecting system 2 to the signal processing and control system 28, as shown in FIG. 9. The signals from conversion system 27 follow to the detecting means 29 via the signal processing and control system 28. The conversion system 27 can provide the conversion of the received signals to the form, acceptable for further processing.

The processed signals control the detecting means, 29, which, for example, starts to assay environment (specimen), analyze, process the result(s) of the analysis, form data containing information about analyzed environment (e.g. temperature, particle concentration, size, quantity, etc.). The appropriately processed by 28 and conversed by 27 data (information) is transmitted by a wireless transmitting means 25 of the transmitting-receiving means 1 of the wireless communication system 30 of the environment monitoring system 3 to the remote control system 47, and through the control signal processing means 49 and conversion means 33 (see FIGS. 6*a*, 7) follows to the processing means 4 of the data processing system 11 for final processing. The result(s) can be displayed (e.g. by the displaying means 6 or printed by the printing means 9, etc.) to the operator for consideration and/or can be recorded (e.g. by floppy disk means 7, compact disk means 8, etc.) for later consideration. It is understandable, that the data can include any information/signal(s), for instance, the signal(s) about battery condition (e.g. "low battery" signal if the battery is presented in the environment monitoring system), some alarm (warning) signals (for example, environmental condition warning information/signals, e.g. particle concentration warning, hydrogen concentration alarm, etc.), and other signals, for instance, calibration information/signal(s) communication, etc. The power supply of the some environment monitoring system can be, for example, provided by alternative current source, if appropriate.

According to FIG. 1, the wireless communication system 46 of the remote control system 47 communicates (transmits) with the wireless communication system 30 of the environment monitoring system 3 (referring to FIG. 8, the wireless communication system 46 of the remote control system 47 communicates with the wireless communication systems 39-42 of the appropriate environment monitoring systems 12-15 respectively). The control signal(s) from the remote control system 47 are received by the receiving means (not shown in FIG. 5, but shown as 26 in FIG. 9) of the transmitting-receiving means (not shown in FIG. 5, but shown as 1 in FIG. 9) of the wireless communication system 30 of the environment monitoring system 3 and follow via conversion system 27 of the detecting system 2 to the signal processing and control system 28, as shown in FIG. 9. The processed signals control the detecting means 29, which, for example, starts to assay and analyze the specimen, process the result(s) of the analysis, form data containing information about analyzed environment (e.g. temperature, particle concentration, size, quantity, etc.). The appropriately processed by 28 (see FIG. 9) and conversed by 27 data (information) is transmitted by a wireless transmitting means 25 of the transmitting-receiving means 1 of the wireless communication system 30 of the environment monitoring system 3 to the wireless receiving system 43 of the data processing system 11. The received data (information) from the wireless receiving system 43 follows through the conversion means 33 (see FIGS. 2, 3) to the processing means 4 of the data processing system 11 for final processing. The result(s) can be displayed (e.g. by the displaying means 6 or printed by the printing means 9, etc.) to the operator for consideration and/or can be recorded (e.g. by floppy disk means 7, compact disk means 8, etc.) for later consideration. For example, the processed information (data), containing the characteristics of the assayed environment (air, gas, liquid or water, for instance, etc.), can be displayed for operator in any convenient form such as graphics, diagrams, tables, texts, etc.

As it was mentioned above, the data (information) can include the information (signal/s/), for instance, regarding battery condition (e.g. "low battery" signal if the battery is presented in the environment monitoring system), some alarm (warning) signals (e.g. particle concentration warning, hydrogen concentration alarm, etc.), and other signals. The power supply of the some environment monitoring system can be for example provided by alternative current source, if appropriate.

The environment assaying control means 37 can perform for example, the low power switching functions for the control of the power executive means (not shown) of the environment assaying system 35 (for example, switching on/off the pump, blower, chamber purging means; switching of the particle size rate means, particle flow control means, etc.— not shown). The assaying air or liquid (water) sample (specimen) follows by the tubular 58 (see FIG. 15) and capillary inlet flow means 31 from the environment assaying system 35 to the monitoring means 34 of the detecting means 29. The monitored specimen (e.g. air, etc.) can be, for instance, exhausted by the capillary outlet flow means 44 and extended outlet flow tubular means 68 via outlet filtrating means 69 of the environment assaying system 35 to the outside environment. Each environment monitoring system can operate independently of each other (or, for example, can operate in the assigned order/sequence [not shown], etc).

FIGS. 11-14 illustrate the third improved variant, wherein the environment monitoring apparatus 71 is a portable unit wireless communicating (wireless controlled) by the remote control system 47. The wireless control can be provided by using the ray-control principles, radio control principles, etc.

Figure 17:
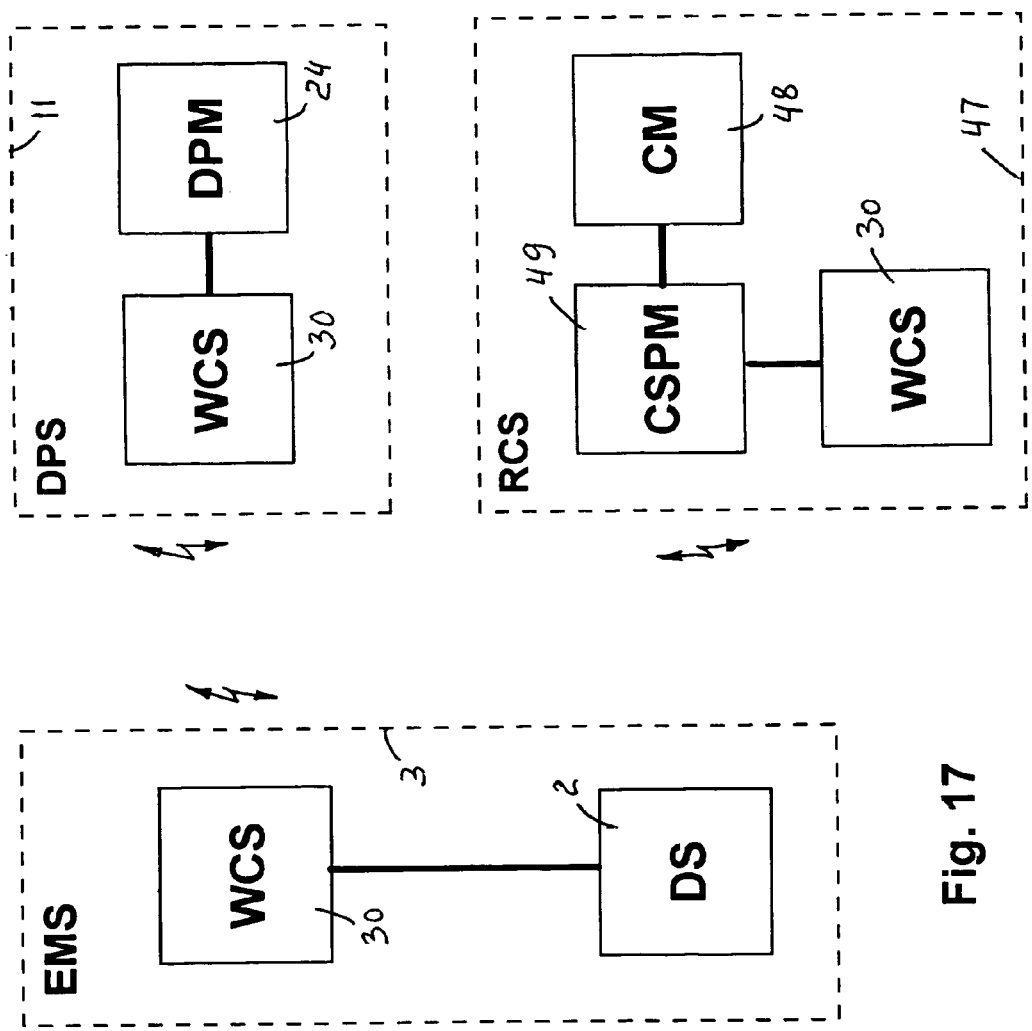
FIG. 17 is a simplified structural block diagram presentation of the fourth wireless communication variant.

Referring to FIG. 17 illustrating the fourth improved variant, each (or at least one) of a plurality of environment monitoring systems (in FIG. 17 is conditionally for simplification shown the single environment monitoring system 3), each (or at least one) of a plurality of data processing systems (in FIG. 17 is conditionally for simplification shown the single data processing system 11), and each (or at least one) of a plurality of remote control systems (in FIG. 17 is conditionally for simplification shown the single remote control system 47) include the wireless communicating system (in FIG. 17 is conditionally for simplification shown the wireless communicating systems 30), but the systems can use non-identical wireless communication system and means /not shown/).

As it was mentioned above, the data can include not only information about at least one of a plurality of characteristics of the environment, but also can include any warning/alarm information/signal(s), for instance, the signal(s) about battery "low" (discharged) condition, etc. In the emergency condition the environment monitoring system(s) can, for example, transmit the final (last) environmental report (information about condition/characteristic(s) of the environment) together with the warning/alarm information/signal(s) before, for instance, to automatically "turn-off" itself, etc.

It should be understood that numerous modifications and variations of the present invention are possible in light of the above teaching and it is also understood, that the above description discloses specific embodiments of the present invention and are for purposes of illustration only without any limitations. There may be other modifications and changes obvious to those of ordinary skill in the art which fall within the scope of the present invention and within scope of the appended claims, the invention may be practiced otherwise than as specifically described herein.

CONCLUSION, RAMIFICATION AND SCOPE

Accordingly the reader will see that, according to the invention, I have provided the effective methods and apparatus for monitoring of environment, for example, such as the air and/or gas, liquid/fluid and/or water or any other environmental substance(s) and/or object(s), e.g. such as the dust on the surface, etc.

The improved methods and apparatus can provide particle (contamination) precise counting and measuring in the assayed environment.

The improved methods and apparatus provide the maximal mobility of the remote sensor(s) (remote environment monitoring system/s/) and remote control(s) (remote control system/s/). This factor may be very convenient for the improved portable apparatus used in the difficult accessible areas of the clean rooms. Also, the improved methods and apparatus increase efficiency and precision of the assayed specimen flow during monitoring.

While the above description contains many specificities, these should not construed as limitations on the scope of the invention, but as exemplification of the presently-preferred embodiments thereof. Many other ramifications are possible within the teaching of the invention.

For example, the improved methods and apparatus can be successfully used for chemical, biological environmental system(s) and apparatus, such as, spectral analyzers and others, where, for example, infrared, ultraviolet, and other ray monitoring principles (e.g., such as X-rays, etc.) can be successfully used instead of the light (laser) beam monitoring principles. Also, the improved methods can be successfully applied to the apparatus using magnetic, electromagnetic, electrostatic fields and/or other types of the fields, or radioactivity instead of the ray(s) and/or light (laser) beam(s).

Thus, the scope of the invention should be determined by the appended claims and their legal equivalents, and not by examples given.

What is claimed is:

1. A method for analysis of an environment monitored by a ray or a light beam, said method, providing a wireless communication, comprises the steps of:

forming in a mobile control system at least one of a plurality of control signals, which provide at least one of a turning-on, turning-off, and/or switching of modes of operation of an environment monitoring system;

converting in said mobile control system said at least one of said plurality of control signals to the form for a wireless transmission;

wireless transmitting said at least one of said plurality of control signals to said environment monitoring system;

wireless receiving of the transmitted at least one of said plurality of control signals by said environment monitoring system;

converting the received at least one of said plurality of control signals to an appropriate form for control of said environment monitoring system;

sensing by a detecting means of said environment monitoring system a light or a pattern created under influence of said light beam or said ray within a monitoring region, and providing an output which is effectively indicative of at least one of a plurality of characteristics of said environment including particle measurement and count;

processing said output in said environment monitoring system;

forming in said environment monitoring system a data, containing an information about said at least one of said plurality of characteristics of said environment and/or a warning and/or an alarm information or at least one warning and/or alarm signal;

converting said data, containing said information about said at least one of said plurality of characteristics of said environment and/or said warning and/or said alarm information or at least one said warning and/or said alarm signal, to a wirelessly transmissible form;

wireless transmitting of the converted data, containing said information about said at least one of said plurality of characteristics of said environment and/or said warning and/or said alarm information or at least one said warning and/or said alarm signal, from said environment monitoring system to a data processing system separate from said mobile control system;

wireless receiving of the transmitted data, containing said at least one of said plurality of characteristics of said environment and/or said warning and/or said alarm information or at least one said warning and/or said alarm signal, by said data processing system;

converting the received data, containing said at least one of said plurality of characteristics of said environment and/or said warning and/or said alarm information or at least one said warning and/or said alarm signal, to the form for processing;

processing the converted data, containing said at least one of said plurality of characteristics of said environment and/or said warning and/or said alarm information or at least one said warning and/or said alarm signal, by said data processing system.

2. The method of claim 1, wherein said environment in said environment monitoring system, which is wirelessly controlled by said mobile control system, is further monitored by a magnetic field and/or an electromagnetic field and/or an electrical field and/or an electrostatic field and/or a radioactivity, and wherein said environment monitoring system further provides said sensing of said pattern created under said influence of said magnetic field and/or said electromagnetic field and/or said electrical field and/or said electrostatic field and/or said radioactivity.

3. The method of claim 1, wherein said wireless transmission from said mobile control system to said environment monitoring system is further provided by an adequate ray or by an adequate light beam.

4. The method of claim 1, wherein said appropriate wireless transmission from said environment monitoring system, which is wirelessly controlled by said mobile control system, to said data processing system is further provided by an adequate ray or by an adequate light beam.

5. A method for analysis of an environment monitored by a ray or a light beam, said method, providing a wireless communication, comprises the steps of:

forming in a mobile control system at least one of a plurality of control signals, which provide at least one of a turning-on, turning-off, and/or switching of modes of operation of an environment monitoring system;

converting in said mobile control system said at least one of said plurality of control signals to a form for a wireless transmission;

wireless transmitting said at least one of said plurality of control signals to said environment monitoring system;

wireless receiving of the transmitted at least one of said plurality of control signals by said environment monitoring system;

converting in said mobile control system the received at least one of said plurality of control signals to an appropriate form for control of said environment monitoring system;

sensing by a detecting means of said environment monitoring system a light or a pattern created under influence of said light beam or said ray within a monitoring region, and providing an output which is effectively indicative of at least one of a plurality of characteristics of said environment including particle measurement and count;

processing said output in said environment monitoring system forming a data, containing an information about said at least one of said plurality of characteristics of said environment and/or a warning and/or an alarm information or at least one warning and/or alarm signal; processing the formed data, containing said at least one of said plurality of characteristics of said environment and/or said warning and/or said alarm information or at least one said warning and/or said alarm signal, by a data processing system of the environment monitoring system;

displaying and/or printing and/or recording the processed data.

6. The method of claim 5, wherein said environment in said environment monitoring system, which is wirelessly controlled by said mobile control system, is further monitored by a magnetic field and/or an electromagnetic field and/or an electrical field and/or an electrostatic field and/or a radioactivity, and wherein said environment monitoring system further provides said sensing of said pattern created under said influence of said magnetic field and/or said electromagnetic field and/or said electrical field and/or said electrostatic field and/or said radioactivity.

7. The method of claim 5, wherein said wireless transmission from said mobile control system to said environment monitoring system is further provided by an adequate ray or by an adequate light beam.

8. An apparatus for analysis of an environment monitored by a ray or light beam, said apparatus, providing a wireless communication, comprises:

at least one of a plurality of mobile control systems said at least one or each of which includes a control means forming at least one of a plurality of control signals;

a wireless transmitting means providing a wireless transmission of at least one of a plurality of control signals;

a control signal processing means connected to said control means and to said wireless transmitting means;

at least one of a plurality of environment monitoring systems, said at least one or each of which includes a detecting system comprising a detecting means including an environment assaying system coupled by a tubular means with a monitoring means providing a sensing of a light or a pattern created under influence of said light beam or said ray within a monitoring region, and providing an output which is effectively indicative of at least one of a plurality of characteristics of an environment including particle measurement and count;

a signal processing and control system comprising an initial signal processing means providing processing of said output from said monitoring means of said detecting means, an environment assaying and control means providing control of said environment assaying system;

a signal and data processing and control system, providing a processing of the processed output, forming a data, containing an information about said at least one of said plurality of characteristics of said environment and/or a warning or an alarm information or at least one warning or alarm signal, and control of the means and systems of said signal processing and control system;

a conversion system, converting said at least one of said plurality of control signals to a form for control of said environment monitoring system, and converting said data, containing said information about said at least one of said plurality of characteristics of said environment and/or said warning or said alarm information or at least one said warning or said alarm signal, by said data processing system, to the form for wireless transmission;

an appropriate wireless communication system comprising an appropriate wireless transmitting-receiving means including an appropriate wireless receiving means providing an appropriate receiving of said at least one of said plurality of control signals;

an appropriate wireless transmitting means providing an appropriate wireless transmission of said data, containing said information about said at least one of said plurality of characteristics of said environment and/or said warning or said alarm information or at least one said warning or said alarm signal;

at least one of a plurality of data processing systems, said at least one or each of which includes an adequate wireless receiving means providing wireless receiving of said data, containing said information about said at least one of said plurality of characteristics of said environment and/or said warning or said alarm information or at least one said warning or said alarm signal;

a data processing means comprising a processing means for processing of the received data, containing said information about said at least one of said plurality of characteristics of said environment and/or said warning or said alarm information or at least one said warning or said alarm signal;

a conversion means connected to said processing means;

a terminal means, connected to said processing means, including at least one of a displaying means, a floppy disk means, a compact disk means, a printing means, a control panel.

9. The apparatus of claim 8, wherein said environment in said at least one of said plurality of environment monitoring systems is, which is wirelessly controlled by said at least one of said plurality of said mobile control systems, is further monitored by a magnetic field and/or an electromagnetic field and/or an electrical field and/or an electrostatic field and/or a radioactivity, and wherein said environment monitoring system further provides said sensing of said pattern created under said influence of said magnetic field and/or said electromagnetic field and/or said electrical field and/or said electrostatic field and/or said radioactivity.

10. The apparatus of claim 8, wherein said wireless transmission from said at least one of said plurality of mobile control systems to said at least one of said plurality of environment monitoring systems is further provided by an adequate ray or by an adequate light beam.

11. The apparatus of claim 8, wherein said appropriate wireless transmission from said at least one of said plurality of environment monitoring systems to said at least one of said plurality of data processing systems is further provided by an adequate ray or by an adequate light beam.

12. The apparatus of claim 8, wherein said apparatus further comprises said at least one of said plurality of said mobile control systems and at least one of a plurality of a portable environment monitoring systems, and wherein each or said at least one of said plurality of said portable environment monitoring systems includes said detecting system comprising said detecting means including said environment assaying system coupled by said tubular means with said monitoring means providing said sensing of said light or said pattern created under influence of said light beam or said ray within said monitoring region, and providing said output which is effectively indicative of said at least one of said plurality of characteristics of said environment; said signal processing and control system comprising said initial signal processing means providing processing of said output from said monitoring means of said detecting means; said environment assaying and control means providing control of said environment assaying system; said signal and data processing and control system, providing said processing of said processed output, forming said data, containing said information about said at least one of said plurality of characteristics of said environment, and control of the means and systems of said signal processing and control system; said conversion system, converting said at least one of said plurality of control signals to a form for control of said at least one of said plurality of said environment monitoring systems; an appropriate wireless communication system comprising an appropriate wireless receiving means providing an appropriate receiving of said at least one of said plurality of control signals; a data processing systems including a data processing means comprising said processing means connected to said terminal means for processing of the formed data, containing said information about said at least one of said plurality of characteristics of said environment and/or said warning or said alarm information or at least one said warning or said alarm signal; said terminal means including at least one of said displaying means, said floppy disk means, said compact disk means, said printing means, said control panel.

13. The apparatus of claim 12, wherein an environment in said at least one or each of said portable environment is, which is wirelessly controlled by said at least one of said plurality of said mobile control systems, is further monitored by a magnetic field and/or an electromagnetic field and/or an electrical field and/or an electrostatic field and/or a radioactivity, and wherein said environment monitoring system further provides said sensing of said pattern created under said influence of said magnetic field and/or said electromagnetic field and/or said electrical field and/or said electrostatic field and/or said radioactivity.

14. The apparatus of claim 12, wherein a wireless transmission of said at least one of said plurality of control signals from said at least one of said plurality of mobile control systems to said at least one of said plurality of said portable environment monitoring systems is provided by an adequate ray or by an adequate light beam.

* * * * *

UNITED STATES PATENT AND TRADEMARK OFFICE
CERTIFICATE OF CORRECTION

PATENT NO. : 7,439,855 B1
APPLICATION NO. : 11/128780
DATED : October 21, 2008
INVENTOR(S) : Aleksandr L. Yufa It is certified that error appears in the above-identified patent and that said Letters Patent is hereby corrected as shown below:

<u>Title page, Item [54] and Column 1, line 1,</u>
Title, change "METHOD" to --METHODS--.

<u>Column 1,</u>
Line 1, change "METHOD" to --METHODS--.

<u>Column 5,</u>
Line 11, change "system and a remote" to --system, and a remote--.
Lines 32, 37, change "conversed" to --converted--.

<u>Column 7,</u>
Line 7, change "means 49 and" to --means 49, and--.
Line 30, change "turn-off and" to --turn-off, and--.
Lines 38, 57, 65, change "conversing" to --converting--.
Lines 40, 60, change "conversed" to --converted--.
Line 44, change "versing" to --verting--.

<u>Column 8,</u>
Line 1, change "conversed" to --converted--.
Line 42, change "king" to --kind--.

<u>Column 9,</u>
Line 19, change "describe" to --described--.
Lines 44, 62, change "conversing" to --converting--.
Line 46, change "conversed" to --converted--.
Line 50, change "versing" to --verting--.
Line 65, change "versed" to --verted--.

<u>Column 10,</u>
Lines 6, 42, change "conversing" to --converting--.
Line 9, change "conversed" to --converted--.

UNITED STATES PATENT AND TRADEMARK OFFICE
CERTIFICATE OF CORRECTION

| | |
|---|---|
| PATENT NO. | : 7,439,855 B1 |
| APPLICATION NO. | : 11/128780 |
| DATED | : October 21, 2008 |
| INVENTOR(S) | : Aleksandr L. Yufa |

It is certified that error appears in the above-identified patent and that said Letters Patent is hereby corrected as shown below:

Column 11,
Line 18, change "be used to" to --be used too--.
Lines 43, 48, change "conversing" to --converting--.
Line 45, change "conversed" to --converted--.
Line 66, change "operate" to --operates--.
Line 67, change "follow" to --follows--.

Column 14,
Line 61, change "conversed" to --converted--.

Column 15,
Line 36, change "conversed" to --converted--.

Column 18,
Line 24, change "transmis-" to --transmitting said at least one of said plurality of control signals--.
Line 25, delete "sion".
Line 28, change "said appropriate" to --said--.
Line 29, change "transmission" to --transmitting of the converted data, containing said information about said at least one of said plurality of characteristics of said environment and/or said warning and/or said alarm information or at least one said warning and/or said alarm signal--.
Line 48, change "in said mobile control system" to --in said environment monitoring system--.

Column 19,
Line 16, change "transmis-" to --transmitting said at least one of said plurality of control signals--.
Line 17, delete "sion".

UNITED STATES PATENT AND TRADEMARK OFFICE
CERTIFICATE OF CORRECTION

PATENT NO.         : 7,439,855 B1
APPLICATION NO. : 11/128780
DATED                 : October 21, 2008
INVENTOR(S)       : Aleksandr L. Yufa It is certified that error appears in the above-identified patent and that said Letters Patent is hereby corrected as shown below:

Column 21,
Line 15, change "systems; an appro-" to --systems;--.
Line 16, delete "priate wireless communication system" and change "comprising an" to --said--.
Line 17, change "providing an" to --providing said--.
Line 19, change "a data processing system including a" to --said--.
Line 20, delete "connected to said".
Line 21, delete "terminal means".

Column 22,
Line 4, after "panel" insert --connected to said processing means--.
Line 5, change "an environment" to --said environment--.
Line 6, change "is" to --monitoring systems--.

Signed and Sealed this

Seventh Day of July, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,439,855 B1 |
| APPLICATION NO. | : 11/128780 |
| DATED | : October 21, 2008 |
| INVENTOR(S) | : Aleksandr L. Yufa |

Page 1 of 1

It is certified that error appears in the above-identified patent and that said Letters Patent is hereby corrected as shown below:

Column 5, Line 8, change "such particle" to --such as particle--.

Column 20, Line 59, change "of a portable" to --of portable--.

Signed and Sealed this

Eighth Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,439,855 B1 | Page 1 of 1 |
| APPLICATION NO. | : 11/128780 | |
| DATED | : October 21, 2008 | |
| INVENTOR(S) | : Aleksandr L. Yufa | |

It is certified that error appears in the above-identified patent and that said Letters Patent is hereby corrected as shown below:

Column 1, Line 5, change "such particle" to --such as particle--.

Column 19, Line 42, change "an environment" to read --said environment--.

Column 20, Line 59, change "of a portable" to --of portable--.

This certificate supersedes the Certificate of Correction issued September 8, 2009.

Signed and Sealed this

Thirteenth Day of April, 2010

David J. Kappos
*Director of the United States Patent and Trademark Office*